US012097620B2

(12) United States Patent
Tan et al.

(10) Patent No.: US 12,097,620 B2
(45) Date of Patent: Sep. 24, 2024

(54) SYSTEMS AND METHODS FOR ENVIRONMENT-ADAPTIVE ROBOTIC DISINFECTION

(71) Applicant: UNIVERSITY OF TENNESSEE RESEARCH FOUNDATION, Knoxville, TN (US)

(72) Inventors: Jindong Tan, Knoxville, TN (US); Da Hu, Louisville, TN (US); Qiang He, Knoxville, TN (US); Shuai Li, Knoxville, TN (US)

(73) Assignee: University of Tennesse Research Foundation, Knoxville, TN (US)

( * ) Notice: Subject to any disclaimer, the term of this patent is extended or adjusted under 35 U.S.C. 154(b) by 357 days.

(21) Appl. No.: 17/445,898

(22) Filed: Aug. 25, 2021

(65) Prior Publication Data
US 2023/0021486 A1 Jan. 26, 2023

Related U.S. Application Data

(60) Provisional application No. 63/222,071, filed on Jul. 15, 2021.

(51) Int. Cl.
*B25J 9/16* (2006.01)
*A61L 2/24* (2006.01)
(Continued)

(52) U.S. Cl.
CPC ............... *B25J 9/1664* (2013.01); *A61L 2/24* (2013.01); *B25J 9/161* (2013.01); *B25J 9/1669* (2013.01);
(Continued)

(58) Field of Classification Search
CPC ..... B25J 9/02; B25J 9/162; B25J 9/161; B25J 9/1669; B25J 9/1664; B25J 5/007;
(Continued)

(56) References Cited

U.S. PATENT DOCUMENTS 11,407,118 B1 * 8/2022 Augenbraun ........... B25J 9/1612
11,717,587 B2 * 8/2023 Trevor ................... B25J 9/1674
700/245
(Continued)

FOREIGN PATENT DOCUMENTS

CN 112588764 * 4/2021 ......... G06F 18/2415

OTHER PUBLICATIONS

English translation of Chinese foreign document CN112588764 (Year: 2021).*

*Primary Examiner* — Russell Frejd
*Assistant Examiner* — Brandon Z Willis
(74) *Attorney, Agent, or Firm* — FisherBroyles, LLP; James Pohl

(57) ABSTRACT

Provided are methods and apparatus for environment-adaptive robotic disinfecting. In an example, provided is a method that can include (i) creating, from digital images, a map of a structure; (ii) identifying a location of a robot in the structure; (iii) segmenting, using a machine learning-based classifying algorithm trained based on object affordance information, the digital images to identify potentially contaminated surfaces within the structure; (iv) creating a map of potentially contaminated surfaces within the structure; (v) calculating a trajectory of movement of the robot to move the robot to a location of a potentially contaminated surface in the potentially contaminated surfaces; and (vi) moving the robot along the trajectory of movement to position a directional decontaminant source adjacent to the potentially contaminated surface. Other methods, systems, and computer-readable media are also disclosed.

22 Claims, 20 Drawing Sheets

(51) Int. Cl.
*B25J 5/00* (2006.01)
*B25J 15/00* (2006.01)
*G06F 18/214* (2023.01)
*G06V 10/25* (2022.01)
*G06V 20/20* (2022.01)

(52) U.S. Cl.
CPC ...... *B25J 15/0019* (2013.01); *G06F 18/2148* (2023.01); *G06V 10/25* (2022.01); *G06V 20/20* (2022.01); *A61L 2202/14* (2013.01); *A61L 2202/16* (2013.01); *B25J 5/007* (2013.01)

(58) Field of Classification Search
CPC .. B25J 15/0019; B25J 11/008; B25J 11/0085; A61L 2/10; A61L 2/24; A61L 2/00; A61L 2202/14; A61L 2202/16; A61L 2202/25; G06F 18/2148; G06V 10/25; G06V 10/255; G06V 10/26; G06V 20/20; G06V 40/10; G05D 1/0212; G05D 1/0246; G05D 1/0274; G05D 2201/0203; G05B 2219/40298; G05B 2219/40519; G05B 2219/40518
See application file for complete search history.

(56) References Cited

U.S. PATENT DOCUMENTS

| | | | |
|---|---|---|---|
| 2019/0160668 A1* | 5/2019 | Oyama | B25J 13/084 |
| 2020/0218274 A1* | 7/2020 | Lee | G06V 20/10 |
| 2021/0181716 A1* | 6/2021 | Quinlan | G06V 10/40 |
| 2022/0211236 A1* | 7/2022 | Yang | G05D 1/0214 |

* cited by examiner

ANNOTATED IMAGE (RED (SEAT BASE-SIT); YELLOW (FLOOR-WALK); GREEN (DOORKNOB-PULL))

ORIGINAL

```
PSEUDO-CODE FOR SEMANTIC FUSION
FUNCTION FUSION (SEM_1, SEM_2)
    IF SEM_1.COLOR IS SEM_2.COLOR THEN
        SEM_FUSION.COLOR = SEM_2.COLOR
        SEM_FUSION.PROBABILITY = (SEM_1.PROBABILITY + SEM_2.PROBABILITY)/2
    ELSE
        IF SEM_1.PROBABILITY < SEM_2.PROBABILITY THEN
            SEM_FUSION = SEM_2
        ELSE
            SEM_FUSION = SEM_1
        SEM_FUSION.PROBABILITY = 0.9 x SEM_FUSION.PROBABILITY
RETURN SEM_FUSION
```

FIG. 10

SYSTEMS AND METHODS FOR ENVIRONMENT-ADAPTIVE ROBOTIC DISINFECTION

CROSS-REFERENCE TO RELATED APPLICATION

This application claims the benefit of U.S. Provisional Patent Application No. 63/222,071, titled "SEGMENTING AREAS OF POTENTIAL CONTAMINATION FOR ADAPTIVE ROBOTIC DISINFECTION IN BUILT ENVIRONMENTS", filed Jul. 15, 2021, the disclosure of which is incorporated herein by reference in its entirety.

STATEMENT REGARDING FEDERALLY SPONSORED RESEARCH

This invention was made with United States Government support under Grants Nos. 2038967, 1952140, and 2026719 awarded by the United States National Science Foundation (NSF). The United States Government has certain rights in the invention.

FIELD OF DISCLOSURE

This disclosure relates generally to the technical field of electronics, and more specifically, but not exclusively, to methods and apparatus for adapting robotic disinfection to specific physical environments.

BACKGROUND

Diseases caused by microbial pathogens have long plagued humanity and are responsible for over 400 million years of potential life lost (a measure of premature mortality) annually across the globe. Mass-gathering built environments such as hospitals, schools, and airports can become hot spots for microbial pathogen colonization, transmission, and exposure, spreading infectious diseases among people in communities, cities, nations, and worldwide. The outbreaks of infectious diseases impose huge burdens on our society. For instance, with more than 200 million people infected and more than 4 million killed (as of Aug. 14, 2021), the pandemic of the coronavirus disease 2019 (COVID-19) continues to impose a staggering infection and death toll. In addition, the epidemic of flu costs the United States' healthcare system an average of $11.2 billion each year. During the 2019-2020 flu season, it was estimated that 24,000 to 62,000 people would die because of flu. Each year, there are about 1.7 million hospital-acquired infections in the United States, resulting in 99,000 related deaths. The disastrous impacts of infections on the society and economy are enormous, highlighting the urgency for developing effective means to mitigate the spread of infectious pathogens in built environments.

Suggested by the World Health Organization (WHO) and the Centers for Disease Control and Prevention (CDC), frequent cleaning and disinfection are critical for preventing pathogen transmission and exposure to slow down the spread of infectious diseases. For instance, during the pandemic of COVID-19, 472 subway stations in New York City were disinfected overnight by workers after a second confirmed COVID-19 case in New York. Deep cleanings are also conducted for school buildings during the closures. Now, disinfection is routine and necessary for all mass-gathering facilities, including schools, airports, transit systems, and hospitals. However, this manual process is labor-intensive, time-consuming, and health-undermining, limiting the effectiveness and efficiency of disinfection. First, pathogens can survive on a variety of surfaces for a long period of time. For example, norovirus and influenza A virus were found on objects with frequent human contacts in elementary school classrooms. The coronavirus that causes severe acute respiratory syndrome (SARS) can persist on nonporous surfaces such as plastics for up to 9 days. Second, pathogens spread very quickly within built environments. It was found that contamination of a single doorknob or tabletop can further contaminate commonly touched objects and infect 40-60% of people in the facilities. Hence, cleaning and disinfection workers are burdened by heavy workloads and subject to high infection risks. Third, workers could be harmed by the chemicals and devices used for disinfection. For instance, nurses who regularly clean surfaces with some disinfectants were found to be at a higher risk of chronic obstructive pulmonary disease. Exposure to some disinfectants was also found to cause asthma. Therefore, there is a critical need for an automated process for indoor disinfection to replace human workers from such labor-intensive and high-risk work.

Accordingly, there are previously unaddressed and long-felt industry needs for methods and apparatus which improve upon conventional methods and apparatus.

SUMMARY

In an example, a computer-implemented method for environment-adaptive robotic disinfecting, where at least a portion of the method being performed by a computing device including at least one physical processor, can include: (i) initiating creating a map, in three dimensions and from digital images, of at least a portion of a structure; (ii) initiating identifying a first location, from the digital images, of a robot in the structure; (iii) initiating segmenting, by the physical processor and using a machine learning-based classifying algorithm, the digital images to identify potentially contaminated surfaces located in the at least the portion of the structure, where the machine learning-based classifying algorithm can be trained with training data including: (a) images of object surfaces known to be potentially contaminated and (b) respective predictor weights that are: (I) respectively associated with the images of the object surfaces and (II) based on object affordance information identifying respective levels of potential contamination of the object surfaces depicted in the images of the object surfaces known to be potentially contaminated; (iv) initiating creating a map of the potentially contaminated surfaces within the structure; (v) initiating calculating a trajectory of movement of at least a portion of the robot to move the at least the portion of the robot to a location of at least a portion of the potentially contaminated surfaces, where the trajectory of movement can be calculated from the map of the at least the portion of the structure, the first location of the robot in the structure, and the map of the potentially contaminated surfaces within the structure; and (vi) initiating movement by the at least the portion of the robot along the trajectory of movement to position a directional decontaminant source adjacent to the location of the at least the portion of the potentially contaminated surfaces.

In some embodiments, the computer-implemented method can further include initiating training the machine learning-based classifying algorithm with the training data.

In some embodiments, the training data can include digital information describing images of object surfaces known to be potentially contaminated in the at least the portion of the structure.

In some examples, (i) the trajectory of the movement can be configured to move the robot from the first location of the robot in the structure to a second location of the robot in the structure and (ii) the second location of the robot in the structure can be within an effective disinfecting range of the directional decontaminant source relative to at least one potentially contaminated surface in the potentially contaminated surfaces.

In some embodiments, the calculating the trajectory of the movement of the at least the portion of the robot can further include calculating the trajectory of the movement from digital information indicating waypoints along a path to be following by an end-effector of the robot.

In some embodiments, the computer-implemented method can further include receiving a user input directing the robot to at least one of: (i) disinfect a specific area in the structure or (ii) perform the initiating creating the map of the at least the portion of the structure at a specific time.

In some embodiments, the computer-implemented method can further include: (i) receiving information indicating present physical contact between a human and the robot and (ii) initiating stopping, responsive to the information indicating present physical contact, the movement by the at least the portion of the robot.

In one embodiment, apparatus configured to perform environment-adaptive robotic disinfecting can include a physical processor and a physical memory communicably coupled to the physical processor and storing instructions configured to cause the physical processor to: (i) initiate creating a map, in three dimensions and from digital images, of at least a portion of a structure; (ii) initiate identifying a first location, from the digital images, of a robot in the structure; (iii) initiate segmenting, using a machine learning-based classifying algorithm, the digital images to identify potentially contaminated surfaces located in the at least the portion of the structure, where the machine learning-based classifying algorithm can be trained with training data including: (a) images of object surfaces known to be potentially contaminated and (b) respective predictor weights that are: (I) respectively associated with the images of the object surfaces and (II) based on object affordance information identifying respective levels of potential contamination of the object surfaces depicted in the images of the object surfaces known to be potentially contaminated; (iv) initiate creating a map of the potentially contaminated surfaces within the structure; (v) initiate calculating a trajectory of movement of at least a portion of the robot to move the at least the portion of the robot to a location of at least a portion of the potentially contaminated surfaces, where the trajectory of movement can be calculated from the map of the at least a portion of the structure, the first location of the robot in the structure, and the map of the potentially contaminated surfaces within the structure; and (vi) initiate movement by the at least the portion of the robot along the trajectory of movement to position a directional decontaminant source adjacent to the location of the at least the portion of the potentially contaminated surfaces.

In some examples, the memory can further store instructions configured to cause the processor to initiate training the machine learning-based classifying algorithm with the training data.

In some embodiments, the training data can include digital information describing images of object surfaces known to be potentially contaminated in the at least the portion of the structure.

In some examples, (i) the trajectory of the movement can be configured to move the robot from the first location of the robot in the structure to a second location of the robot in the structure and (ii) the second location of the robot in the structure can be within an effective disinfecting range of the directional decontaminant source relative to at least one potentially contaminated surface in the potentially contaminated surfaces.

In some examples, the calculating the trajectory of the movement of the at least the portion of the robot further can include calculating the trajectory of the movement from digital information indicating waypoints along a path to be following by an end-effector of the robot.

In some embodiments, the memory can further store instructions configured to cause the processor to receive a user input directing the robot to at least one of: (i) disinfect a specific area in the structure or (ii) perform the initiating creating the map of the at least the portion of the structure at a specific time.

In an example, the memory can further store instructions configured to cause the processor to: (i) receive information indicating present physical contact between a human and the robot and (ii) initiate stopping, responsive to the information indicating present physical contact, the movement by the at least the portion of the robot.

In some embodiments, the physical processor can be at least one of a microprocessor, a microcontroller, a digital signal processor, a field programmable gate array, a programmable logic device, an application-specific integrated circuit, a controller, a non-generic special-purpose processor, a state machine, a gated logic device, a discrete hardware component, or a dedicated hardware finite state machine.

In some examples, the above-described method can be encoded as computer-readable instructions on a non-transitory computer-readable medium. For example, a computer-readable medium may include one or more computer-executable instructions that, when executed by at least one processor of a computing device, may cause the computing device to: (i) initiate creating a map, in three dimensions and from digital images, of at least a portion of a structure; (ii) initiate identifying a first location, from the digital images, of a robot in the structure; (iii) initiate segmenting, using a machine learning-based classifying algorithm, the digital images to identify potentially contaminated surfaces located in the at least the portion of the structure, where the machine learning-based classifying algorithm can be trained with training data including: (a) images of object surfaces known to be potentially contaminated and (b) respective predictor weights that are: (I) respectively associated with the images of the object surfaces and (II) based on object affordance information identifying respective levels of potential contamination of the object surfaces depicted in the images of the object surfaces known to be potentially contaminated; (iv) initiate creating a map of the potentially contaminated surfaces within the structure; (v) initiate calculating a trajectory of movement of at least a portion of the robot to move the at least the portion of the robot to a location of at least a portion of the potentially contaminated surfaces, where the trajectory of movement can be calculated from the map of the at least a portion of the structure, the first location of the robot in the structure, and the map of the potentially contaminated surfaces within the structure; and (vi) initiate movement by the at least the portion of the robot along the trajectory of movement to position a directional decontaminant source adjacent to the location of the at least the portion of the potentially contaminated surfaces.

In some embodiments, the processor-executable instructions can further include instructions configured to cause the processor to initiate training the machine learning-based classifying algorithm with the training data.

In some examples, the training data can include digital information describing images of object surfaces known to be potentially contaminated in the at least the portion of the structure.

In some embodiments, (i) the trajectory of the movement can be configured to move the robot from the first location of the robot in the structure to a second location of the robot in the structure and (ii) the second location of the robot in the structure can be within an effective disinfecting range of the directional decontaminant source relative to at least one potentially contaminated surface in the potentially contaminated surfaces.

In some examples, the calculating the trajectory of the movement of the at least the portion of the robot can further include calculating the trajectory of the movement from digital information indicating waypoints along a path to be following by an end-effector of the robot.

In some examples, the processor-executable instructions can further include instructions configured to cause the processor to receive a user input directing the robot to at least one of: (i) disinfect a specific area in the structure or (ii) perform the initiating of creating the map of the at least the portion of the structure at a specific time.

In some examples, the processor-executable instructions further include instructions configured to cause the processor to: (i) receive information indicating present physical contact between a human and the robot and (ii) initiate stopping, responsive to the information indicating present physical contact, the movement by the at least the portion of the robot.

Features from any of the embodiments described herein may be used in combination with another embodiment in accordance with the general principles described herein. These and other embodiments, features, and advantages will be more fully understood upon reading this detailed description in conjunction with the accompanying drawings and claims.

BRIEF DESCRIPTION OF THE DRAWINGS

FIG. 10 depicts an example pseudocode for semantic fusion of two different frames.

Figure 1A:
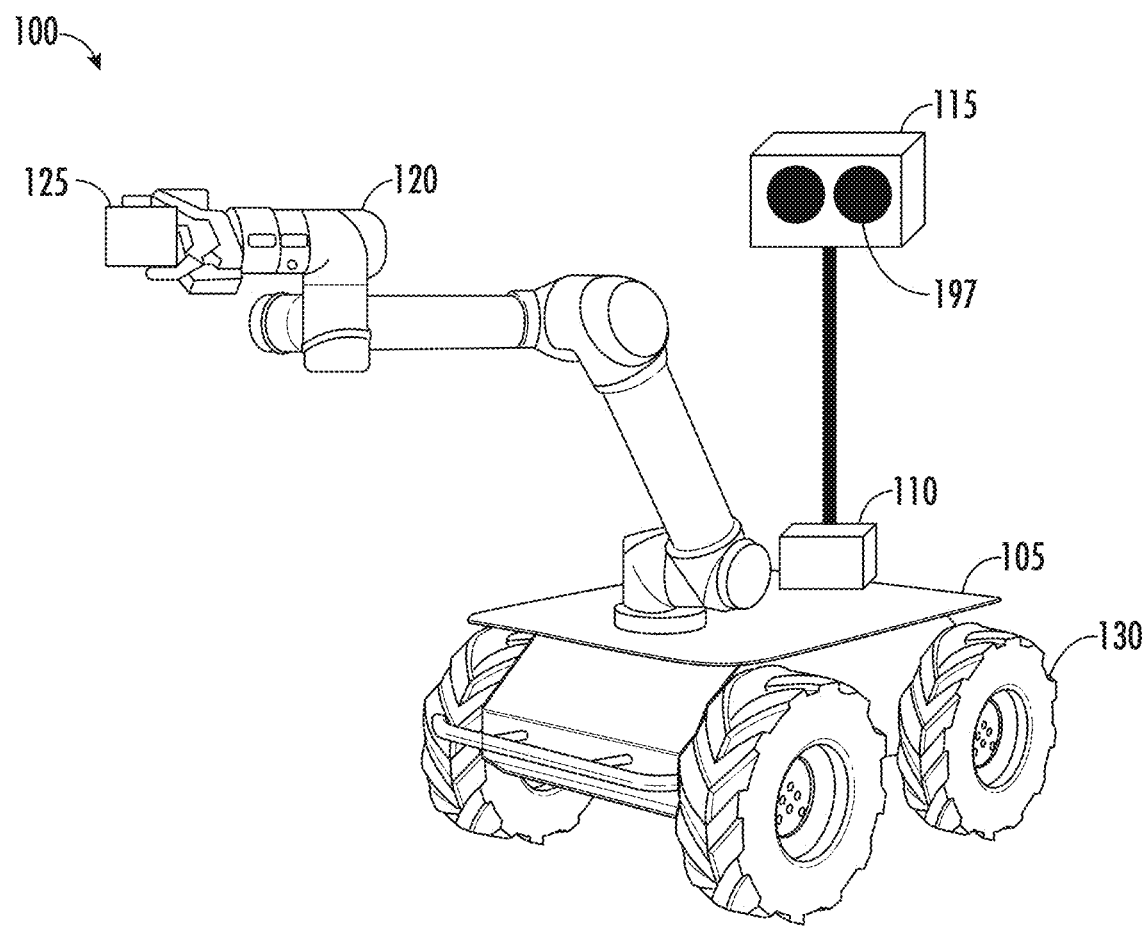
FIG. 1A depicts an example robot suitable for implementing examples of the disclosed subject matter.

Each of the drawings is provided for illustration and description only and does not limit the present disclosure. In accordance with common practice, the features depicted by the drawings may not be drawn to scale. Accordingly, the dimensions of the depicted features may be arbitrarily expanded or reduced for clarity. In accordance with common practice, some of the drawings are simplified for clarity. Thus, the drawings may not depict all components of a particular apparatus or method. Further, like reference numerals denote like features throughout the specification and figures.

DETAILED DESCRIPTION

Provided are example methods and apparatuses which control performing environment-adaptive robotic disinfecting.

The absence of conventional intelligent robotic disinfection technologies stemmed from at least two conventional knowledge gaps. First, there was a lack of a method to enable conventional robots to perceive and map areas of potential contamination in built environments, thus hindering precision disinfection. Second, conventional robots did not adapt their trajectories with respect to different areas of potential contamination for effective and safe disinfection.

To address the previously unaddressed and long-felt industry needs for methods and apparatus which improve upon conventional methods and apparatus, provided are novel frameworks and new algorithms for methods and apparatuses which control performing environment-adaptive robotic disinfecting.

In non-limiting examples, provided are apparatuses and methods configured to enable robotic disinfection in built environments to reduce pathogen transmission and exposure. First, a simultaneous localization and mapping technique can be exploited for robot navigation in built environments. Second, a deep-learning method can segment and map areas of potential contamination in three dimensions based on the object affordance concept. Third, with short-wavelength ultraviolet light, trajectories of robotic disinfection are generated to adapt to geometries of the areas of the potential contamination to provide disinfection.

In another non-limiting example, provided is a robotic manipulator configured to conduct automatic disinfection in indoor environments to reduce pathogen transmission and exposure, and thus potentially prevent outbreaks of infectious diseases. First, a deep-learning method can detect and segment areas of potential contamination. Using a visual Simultaneous Localization and Mapping (SLAM) technique, the segmented areas of potential contamination can be mapped in a three-dimensional (3D) space to guide a robotic disinfection process. Second, a new method can control a robot to move to the areas needing disinfection and generate trajectories for movement of the robot and/or a directional decontaminant source based on geometries of areas of potential contamination, surrounding contexts, or both. The adaptive motion can enhance disinfection quality, safety, or both.

SLAM is a group of techniques that can enable robots to perceive their environments, localize themselves, and build maps for subsequent applications. The SLAM techniques are compatible with robot operating systems (ROS) to allow robot navigation in built environments. For example, GMapping is a ROS SLAM approach that uses a particle filter to create grid maps and estimate robot poses. GMapping and TinySLAM can be used for localization and autonomous navigation. Using two-dimensional light detection and ranging (LiDAR) with low computation resources, Hector SLAM and ethzasl_icp_mapping can provide real-time two-dimensional occupancy mapping. Google Cartographer is an efficient graph-based SLAM approach using portable laser ranger-finders. Maplab and VINS-Mono are graph-based SLAM approaches that fuse the information from an inertial measurement unit and a camera. The RTAB-Map is a complete graph-based SLAM and can be incorporated in a ROS package for various applications. ORB-SLAM2 is a popular feature-based visual SLAM approach that has been adapted to monocular, stereo, and red-green-blue-depth (RGB-D) cameras. In contrast to feature-based algorithms, dense visual odometry DVO-SLAM uses photometric and depth errors over pixels of two consecutive RGB-D images to estimate camera motion.

Robot perception is important for deriving intelligent robot decisions and actions. In environment-adaptive robotic disinfecting applications, robots need to perceive the areas of potential contamination on various objects (e.g., tangible objects located in a structure, a tangible portion of the structure, etc.) for disinfection. Detecting and segmenting the areas of potential contamination from images are related to object detection and semantic segmentation. In addition, the concept of object affordance is also relevant, as for example, detecting a computer on an office desk does not mean that the computer necessarily needs to be disinfected. Conventional techniques lack capabilities to reason which areas, under what circumstances, or both, an object or a part of the object needs specific (e.g., targeted) disinfection. Understanding how humans interact with different objects helps identify areas of potential contamination. For example, high-touch areas are considered to be contagious and should be disinfected. Human interactions with objects have implications on how and which part of objects may be contaminated and could contaminate different parts of human body.

The examples disclosed hereby advantageously address the long-felt industry needs, as well as other previously unidentified needs, and mitigate shortcomings of conventional techniques. In some examples, systems and methods described herein can advantageously improve on conventional disinfecting techniques. In some embodiments, systems and methods described herein can advantageously improve functioning of robots, devices configured to control robots, or both. In some examples, systems and methods described herein can advantageously improve functioning of a robot configured to disinfect a potentially contaminated surface in a structure by providing precisely located disinfecting at a target location while exposing a human (e.g., a patient, a doctor, a nurse) in a structure to little, if any ultraviolet radiation. Thus, humans do not need to leave the structure during the disinfecting process. Precisely locating an decontaminant source closer to a potentially contaminated surface increases efficiency of disinfecting, which can reduce disinfection time. Precisely locating an decontaminant source closer to a potentially contaminated surface reduces a probability that sophisticated and expensive equipment will be damaged during disinfecting.

In some examples, systems and methods described herein can advantageously orient an decontaminant source relative to a specific potentially contaminated surface in a structure and can adapt to changing locations of the potentially contaminated surface in the structure. In a non-limiting example, the systems and methods described herein can adapt motion of a disinfecting robot to a changed location of a wheeled table.

In some examples, systems and methods described herein can advantageously orient an decontaminant source relative to a specific potentially contaminated surface in a structure and can adapt to a presence of a new potentially contaminated surface in the structure. In a non-limiting example, the systems and methods described herein can adapt motion of a disinfecting robot to a wheeled table newly placed in the structure.

In some examples, systems and methods described herein can advantageously adapt to a shape of a potentially contaminated surface in a structure to orient an decontaminant source relative to the potentially contaminated surface. In a non-limiting example, the systems and methods described herein can adapt motion of a disinfecting robot to a shape of a surface of a chair.

In some embodiments, systems and methods described herein can advantageously adapt to a physical interaction between a disinfecting robot and a human by reducing a motion of the disinfecting robot, ceasing the motion of the disinfecting robot, or both.

In some embodiments, systems and methods described herein can advantageously reduce an infection risk of cleaning workers by keeping them away from contaminated areas.

In some examples, systems and methods described herein can advantageously use affordance information to guide a disinfecting robot to focus on extremely contaminated locations (e.g., "hot spots") and thoroughly disinfect potentially contaminated areas.

Numerous examples are disclosed in this application's text and drawings. Alternate examples can be devised without departing from the scope of this disclosure. Additionally, conventional elements of the current teachings may not be described in detail, or may be omitted, to avoid obscuring aspects of the current teachings.

The following list of abbreviations, acronyms, and terms in Table One is provided to assist in comprehending the current disclosure and are not provided as limitations.

TABLE ONE

List of Abbreviations

| Abbreviation | Definition |
| --- | --- |
| AP | Average Precision |
| CNN | Convolutional Neural Network |
| DSC | Dice Coefficient |
| DWA | Dynamic Window Approach |
| IK | Inverse Kinematics |
| IoU | Intersection over Union |
| LTM | Long Term Memory |
| mAP | Average of AP over all classes |
| mDSC | Average of DSC over all classes |
| mIoU | Average of IoU over all classes |
| ROS | Robot Operating System |
| SLAM | Simultaneous Localization and Mapping |
| STM | Short Term Memory |
| UV | Ultraviolet |
| WM | Working Memory |

Figure 1B:
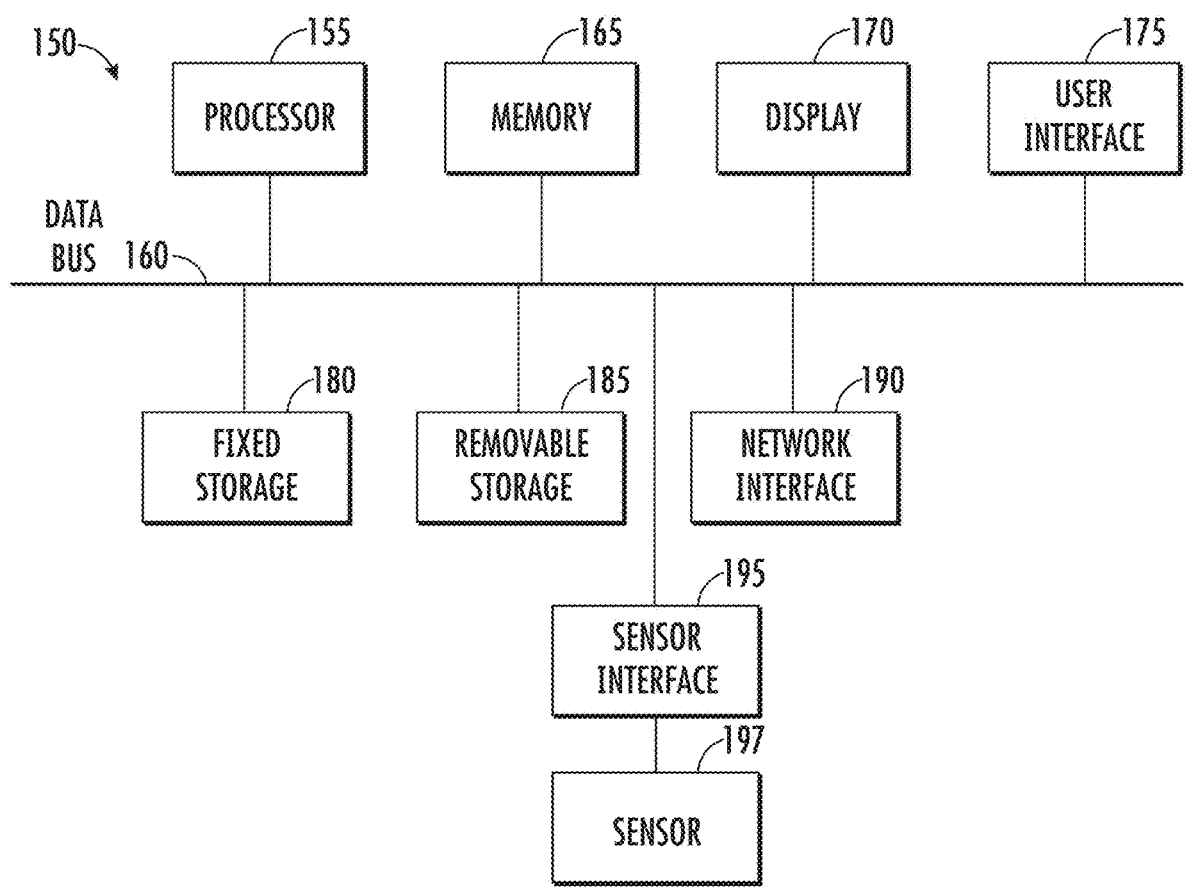
FIG. 1B depicts a block diagram of a computing device suitable for use as a robot controller.

This description provides, with reference to FIGS. 1A-1B, detailed descriptions of example robot apparatus for environment-adaptive robotic disinfecting. Detailed descriptions of an example method for environment-adaptive robotic disinfecting are provided in connection with FIG. 2. FIGS. 3-19 depict non-limiting aspects of example methods that provide intelligent robotic disinfection in built environments, as well as results of experiments.

FIG. 1A depicts a non-limiting example robot 100 suitable for implementing examples of the disclosed subject matter. The robot 100 can include a chassis 105, a robot controller 110, a sensor unit 115, a robotic arm 120, and decontaminant source 125, wheels 130, or a combination thereof. These devices are described in further detail herein.

The chassis 105 can provide a structure to which other components of the robot 100 can be fastened. Components of the robot 100 can be mounted within a cavity defined by a portion of the chassis 105, fastened to an exterior of the chassis 105, or a combination thereof.

The robot controller 110 can be a hardware-implemented computing device having at least one physical processor (e.g., processor 155 in FIG. 1B). The robot controller can receive an input from a sensor (e.g., sensor 197 in FIG. 1B), a sensor interface (e.g., sensor interface 195 in FIG. 1B), a user interface (e.g., user interface 175 in FIG. 1B), a network interface (e.g., network interface 190 in FIG. 1B), or combination thereof. The robot controller 110 can perform an algorithmic operation on the input from the sensor to produce a controller output. In examples, the controller output can be displayed on a display (e.g., display 170 in FIG. 1B). Examples of controller output can initiate movement of an electromechanical device, such as, and not limited to, an electric motor configured to rotate at least one wheel of the wheels 130. Examples of controller output can initiate movement of an electromechanical device, such as, and not limited to, a joint of the robotic arm 120. Further examples of controller output can control an decontaminant source to vary an illumination level provided by the decontaminant source, such as the decontaminant source 125.

In an example, the robot controller 110 can include at least a portion of the computing device 150 in FIG. 1B as at least as a constituent part.

In some examples, the robot controller 110 can initiate performing at least a portion of a method described hereby, perform at least a portion of a method described hereby, or both. In some embodiments, the robot 100 can work in conjunction with computing devices other than the robot controller 110 to initiate performing at least a portion of a method described hereby, to perform at least a portion of a method described hereby, or both.

The sensor unit 115 can be electronic device configured to sense at least one characteristic of an environment within which the robot 100 is located. In examples, the sensor unit 115 can include the sensor 197, the sensor interface 195, or combination thereof. The sensor unit can include a monocular camera, a stereo camera, an RGB-D camera, a two-dimensional light detection and ranging (LiDAR) sensor, a three-dimensional LiDAR sensor, a thermal camera, a radio-frequency identification (RFID) sensor, a radio detection and ranging (Radar) device, or combination thereof.

In some examples, the sensor unit 115 can be attached to the robotic arm 120. For example, the sensor unit 115 can be attached to a robotic arm to enable the robot 100 to move the sensor unit 115 relative to the robot 100. In an example, the sensor unit 115 can be attached to a first robotic arm, while the decontaminant source 125 is attached to a second robotic arm.

The robotic arm 120 can be an electromechanical device configured to move relative to the chassis 105. The robot 100 can include at least one robotic arm 120. The robotic arm 120 can include at least one joint configured to locate an end effector relative to the chassis 105. The robotic arm 120 can include an end effector that is configured to interact with an environment within which the robot 100 is located. For example, the robotic arm 120 can include the decontaminant source 125 as an end effector. The robotic arm 120 can be controlled by the robot controller 110, based on a trajectory of movement, to quickly, efficiently, and accurately locate the decontaminant source 125 adjacent to a potentially contaminated surface. In an example, the robotic arm 120 can locate the decontaminant source 125 in three dimensions. In an example, the robotic arm 120 can have seven degrees of freedom. Thus, decontaminant emitted by the decontaminant source 125 can disinfect the potentially contaminated surface at a close distance from the potentially contaminated surface (e.g., within 10 cm).

During disinfection, a distance between the decontaminant source 125 and a potentially contaminated surface can be related to a geometry of the potentially contaminated surface. This distance can be dynamically determined, adjusted, or both as the robot 100 detects and segments the potentially contaminated surface from the digital images. Maintaining a small distance to the potentially contaminated surface can disinfect the potentially contaminated surface efficiently and avoid directing decontaminant at people standing nearby the robot 100. For example, when the robot 100 detects a potentially contaminated planar surface, such as a portion of a table, the robot 100 can orient a UV light to disinfect that planar surface at a very small distance (e.g., less than 3 cm, such as 1 cm). In contrast, for undulating or irregular potentially contaminated surfaces (e.g., a surface of healthcare equipment), it may be unsafe to keep that close (e.g., 1 cm) to the potentially contaminated surface (e.g., so the robot avoids a collision), thus a slightly larger distance will be maintained (e.g., a distance ranging between 3 cm to 10 cm, inclusive) depending on the curvature of the potentially contaminated surface. The distance between the decontaminant source 125 and a potentially contaminated surface can be dynamically determined, adjusted, or both in response to results of the detection and segmentation of the potentially contaminated surface.

The decontaminant source 125 can be an electrical device, such as an ultraviolet light source, configured to emit ultraviolet light (i.e., ultraviolet radiation). In examples, the decontaminant source 125 can include a low-pressure mercury lamp, an excimer lamp, a pulse xenon lamp, a light-emitting diode, or combination thereof. The decontaminant source 125 can be configured to provide directional ultraviolet light. For example, the decontaminant source 125 can be equipped with a shade, a reflector, or both to limited direction at which ultraviolet light is emitted from the decontaminant source 125. In further example, the decontaminant source 125 can include a housing defining a cavity within which an ultraviolet light emitter is located, where the housing defines a space (e.g., a slit) through which directional ultraviolet light emitted from the ultraviolet light emitter can depart the decontaminant source 125.

In examples, the decontaminant source 125 can be fastened to the robotic arm 120. In other examples decontaminant source 125 can be grasped by a gripper that is an end effector of the robotic arm 120.

In examples, the decontaminant source can be a device configured to direct a liquid disinfectant, an aerosol disinfectant, or both toward a potentially contaminated surface.

The wheels 130 can enable the robot 100 to move within environment of the robot 100. The robot 100 can have at least two or more of the wheels 130. The wheels 130 can be mechanically rotated by a motor controlled by the robot controller 110. In some examples, the wheels 130 may also be mechanically coupled, electrically coupled, or both to a sensor (e.g., the sensor 197) to provide position feedback to the robot controller 110. In some examples, at least one of the wheels 130 can ride upon a continuous track (e.g., a tank-style tread).

FIG. 1B illustrates an example computing device 150 suitable for implementing examples of the disclosed subject matter. For example, the computing device 150 can be suitable for use as the robot controller 110. In examples, aspects of the computing device 150 can be implemented at least in part in a desktop computer, a laptop computer, a server, a mobile device, a special-purpose computer, a non-generic computer, an electronic device described hereby (as is practicable), the like, or a combination thereof. In some examples, the disclosed subject matter can be implemented in, and used with, hardware devices, computer network devices, the like, or a combination thereof. The configuration depicted in FIG. 1B is an illustrative example and is not limiting.

In some examples, the computing device 150 can include a processor 155, a data bus 160, a memory 165, a display 170, a user interface 175, a fixed storage device 180, a removable storage device 185, a network interface 190, a sensor interface 195, a sensor 197, the like, or a combination thereof. These elements are described in further detail herein.

The processor 155 can be a hardware-implemented processing unit configured to control at least a portion of operation of the computing device 150. The processor 155 can perform logical and arithmetic operations based on processor-executable instructions stored within the memory 165. The processor 155 can be configured to execute instructions which cause the processor 155 to initiate at least a part of a method described hereby. In an example, the processor 155 can interpret instructions stored in the memory 165 to initiate at least a part of a method described hereby. In an example, the processor 155 can execute instructions stored in the memory 165 to initiate at least a part of a method described hereby. The instructions, when executed by the processor 155, can transform the processor 155 into a special-purpose processor that causes the processor to perform at least a part of a function described hereby. The processor 155 may also be referred to as a central processing unit (CPU), a special-purpose processor (e.g., a non-generic processor), or both.

In some examples, the computing device 150 can implement machine-learning techniques (e.g., a Convolutional Neural Network (CNN)) to collect information, process information, or both, over time to adapt trajectories of movement of the robot 100 to environments within which the robot 100 can be located. As environments within which the robot 100 is located change, the computing device 150 can learn and adapt over time (e.g., without user intervention). In some examples, information stored in an information storage device of the computing device 150 can be transferred to another computing device 150 (or other type of computing device) and thus negate a need for another machine-learning training cycle.

The processor 155 can comprise or be a component of a physical processing system implemented with one or more processors. In some examples, the processor 155 can be implemented with at least a portion of: a microprocessor, a microcontroller, a digital signal processor (DSP) integrated circuit, a field programmable gate array (FPGA), a programmable logic device (PLD), an application-specific integrated circuit (ASIC), a controller, a state machine, a gated logic circuit, a discrete hardware component, a dedicated hardware finite state machine, a suitable physical device configured to manipulate information (e.g., calculating, logical operations, the like, or a combination thereof), the like, or a combination thereof.

The data bus 160 can couple components of the computing device 150. The data bus 160 can enable information communication between the processor 155 and one or more components coupled to the processor 155. In some examples, the data bus 160 can include a data bus, a power bus, a control signal bus, a status signal bus, the like, or a combination thereof. In an example, the components of the computing device 150 can be coupled together to communicate with each other using a different suitable mechanism.

The memory 165 generally represents any type or form of volatile storage device, non-volatile storage device, medium, the like, or a combination thereof. The memory 165 can store data, processor-readable instructions, the like, or a combination thereof. In an example, the memory 165 can store data, load data, maintain data, or a combination thereof. In an example, the memory 165 can store processor-readable instructions, load processor-readable instructions, maintain processor-readable instructions, or a combination thereof. In some embodiments, the memory 165 can store computer-readable instructions configured to cause a processor (e.g., the processor 155) to initiate performing at least a portion of a method described hereby. The memory 165 can be a main memory configured to store an operating system, an application program, the like, or a combination thereof. The memory 165 can store a basic input-output system (BIOS) which can control basic hardware operation such as interaction of the processor 155 with peripheral components. The memory 165 can also include a non-transitory machine-readable medium configured to store software. Software can mean any type of instructions, whether referred to as at least one of software, firmware, middleware, microcode, hardware description language, the like, or a combination thereof. Processor-readable instructions can include code (e.g., in source code format, in binary code format, executable code format, or in any other suitable code format).

The memory 165 can include at least one of read-only memory (ROM), random access memory (RAM), a flash memory, a cache memory, an erasable programmable read-only memory (EPROM), an electrically erasable programmable read-only memory (EEPROM), a register, a hard disk drive (HDD), a solid-state drive (SSD), an optical disk drive, other memory, the like, or a combination thereof which is configured to store information (e.g., data, processor-readable instructions, software, the like, or a combination thereof) and is configured to provide the information to the processor 155.

The display 170 can include a component configured to visually convey information to a user of the computing device 150. In examples, the display 170 can be a video display screen, such as a light-emitting diode (LED) screen, a touch screen, or both.

The user interface 175 can include user devices such as a switch, a keypad, a touch screen, a microphone, a speaker, an audio production device, a jack for coupling the computing device to an audio production device, the like, or a combination thereof. The user interface 175 can optionally include a user interface controller. The user interface 175 can include a component configured to convey information to a user of the computing device 150, a component configured to receive information from the user of the computing device 150, or both.

The fixed storage device 180 can include one or more hard drive, flash storage device, the like, or a combination thereof. The fixed storage device 180 can be an information storage device which is not configured to be removed during use. The fixed storage device 180 can optionally include a fixed storage device controller. The fixed storage device 180 can be integral with the computing device 150 or can be separate and accessed through an interface.

The removable storage device 185 can be integral with the computing device 150 or can be separate and accessed through other interfaces. The removable storage device 185 can be an information storage device which is configured to be removed during use, such as a memory card, a jump drive, a flash storage device, an optical disk, the like, or a combination thereof. The removable storage device 185 can optionally include a removable storage device controller. The removable storage device 185 can be integral with the computing device 150 or can be separate and accessed through an interface.

In examples, a computer-readable storage medium such as one or more of the memory 165, the fixed storage device 180, the removable storage device 185, a remote storage location, the like, or a combination thereof can store non-transitory computer-executable instructions configured to cause a processor (e.g., the processor 155) to implement at least an aspect of the present disclosure.

The network interface 190 can couple the processor 155 (e.g., via the data bus 160) to a network and enable exchanging information between the processor 155 and the network. In some examples, the network interface 190 can couple the processor 155 (e.g., via the data bus 160) to the network and enable exchanging information between the processor 155 and the sensor 197. For example, the network interface 190 can enable the processor 155 to communicate with one or more other network devices. The network interface 190 can couple to the network using any suitable technique and any suitable protocol. In some examples, the network interface 190 can include a data bus, a power bus, a control signal bus, a status signal bus, the like, or a combination thereof. Example techniques and protocols the network interface 190 can be configured to implement include digital cellular telephone, WiFi™, Bluetooth®, near-field communications (NFC), the like, or a combination thereof.

The network can couple the processor 155 to one or more other network devices. In some examples, the network can enable exchange of information between the processor 155 and the one or more other network devices. In some examples, the network can enable exchange of information between the processor 155 and the sensor 197. The network can include one or more private networks, local networks, wide-area networks, the Internet, other communication networks, the like, or a combination thereof. In some examples, the network can be a wired network, a wireless network, an optical network, the like, or a combination thereof.

In some embodiments, the network device can store computer-readable instructions configured to cause a processor (e.g., the processor 155) to initiate performing at least a portion of a method described hereby. In an example, the one or more other network devices can store non-transitory computer-executable instructions configured to cause a processor (e.g., the processor 155) to implement at least an aspect of the present disclosure. The non-transitory computer-executable instructions can be received by the processor 155 and implemented using at least a portion of techniques described hereby. In another example, information described hereby can be stored in the fixed storage device 180, the removable storage device 185, the network device, the like, or a combination thereof.

The network device can include the sensor 197, a hardware device configured to couple the network to the sensor 197, a server, a digital information storage device, the like, or a combination thereof.

In some examples, the network device can include user devices such as a switch, a keypad, a touch screen, a microphone, a speaker, an audio reproduction device, a jack for coupling the computing device to an audio reproduction device, the like, or a combination thereof. The network device can optionally include a user interface controller. The network device can include a component configured to convey information to a user of the computing device 150, a component configured to receive information from the user of the computing device 150, or both.

The sensor interface 195 can couple the processor 155 (e.g., via the data bus 160) to the sensor 197. In some examples, the sensor interface 195 can couple the processor 155 (e.g., via the data bus 160) to the sensor 197 and enable exchanging information between the processor 155 and the sensor 197. For example, the sensor interface 195 can enable the processor 155 to receive, from the sensor 197, analog information and/or digital information describing at least one characteristic of an environment within which the robot 100 is located. The sensor interface 195 can couple to the sensor 197 using any suitable technique and any suitable protocol. In some examples, the sensor interface 195 can perform analog-to-digital conversion, digital-to-analog conversion, or a combination thereof. In some examples, the sensor interface 195 can include a data bus, a power bus, a control signal bus, a status signal bus, the like, or a combination thereof. Example techniques and protocols the sensor interface 195 can be configured to implement include digital cellular telephone, WiFi™, Bluetooth®, near-field communications (NFC), the like, or a combination thereof.

The sensor 197 can sense a characteristic of an environment in which the robot 100 is located. In examples, the sensor 197 can produce an analog output indicating the at least one state, a digital output indicating the at least one state, or both. The sensor 197 can produce an output of the at least one state using any suitable technique, any suitable protocol, or both. In some examples, the sensor 197 can perform analog-to-digital conversion, digital-to-analog conversion, or a combination thereof. In some examples, the sensor 197 can include a data bus, a power bus, a control signal bus, a status signal bus, the like, or a combination thereof. Example techniques and protocols the sensor 197 can be configured to implement include digital cellular telephone, WiFi™, Bluetooth®, near-field communications (NFC), the like, or a combination thereof.

In examples, the sensor 197 can include a monocular camera, a stereo camera, an RGB-D camera, a two-dimensional light detection and ranging (LiDAR) sensor, a sensor described herein, a sensor configured to produce computer-processable data described herein, or combination thereof.

In some examples, all the components illustrated in FIG. 1B need not be present to practice the present disclosure. Further, the components can be coupled in different ways from those illustrated.

Overview of Example Methods

Figure 2:
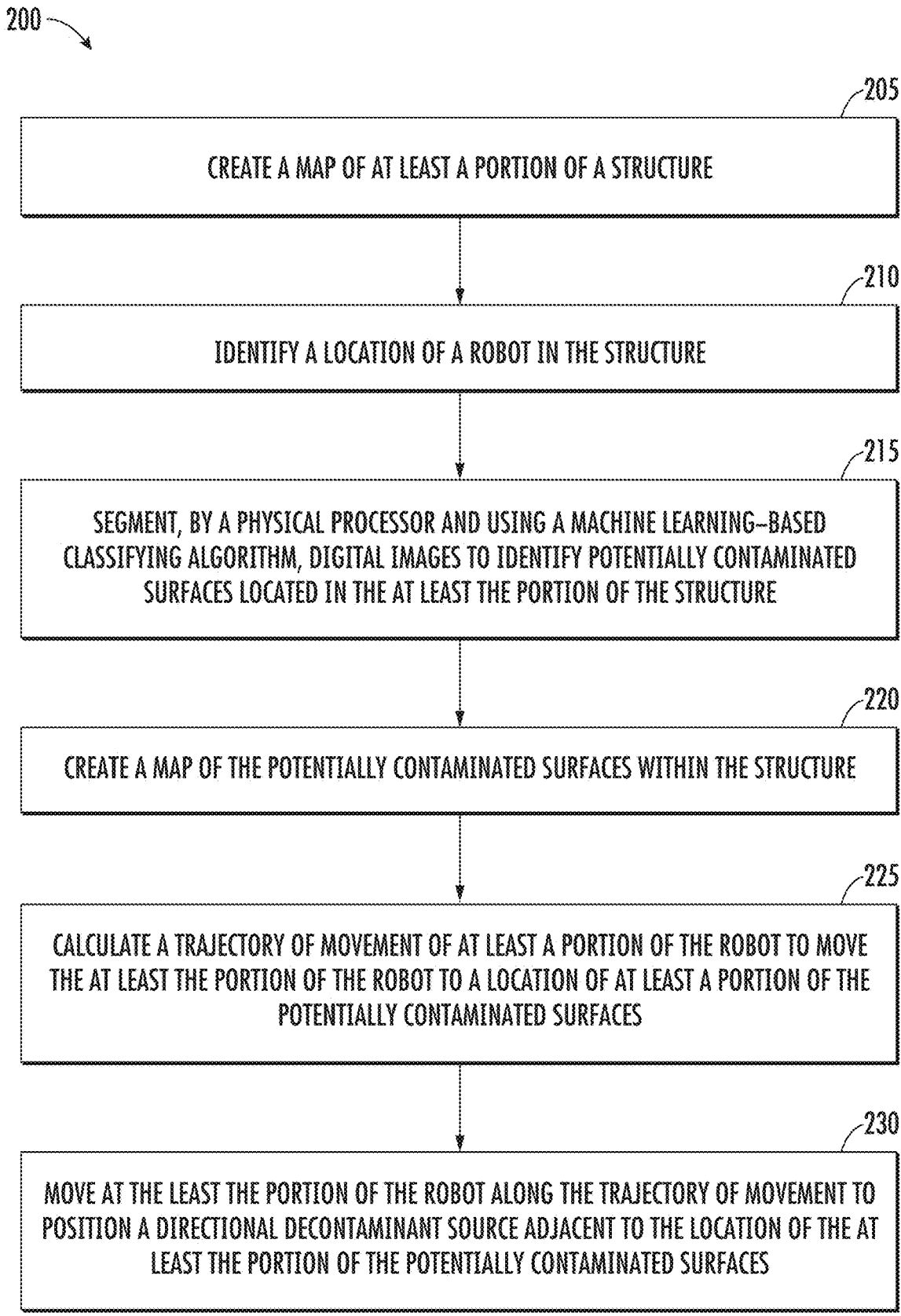
FIG. 2 depicts a block diagram of an example method for environment-adaptive robotic disinfecting.

FIG. 2 depicts a block diagram of an example method for environment-adaptive robotic disinfecting 200. The method 200 can be performed at least in part by the apparatus described hereby, such as the robot controller 110 in FIG. 1A, the computing device 150 in FIG. 1B, or a practicable combination thereof. Additional aspects of example methods for environment adaptive robotic disinfecting are described herein with respect to FIGS. 3-19. These additional aspects can be integrated with the method 200.

As illustrated in FIG. 2, at block 205, one or more of the devices described herein can create a map of at least a portion of a structure. In examples, the map can be a digital representation of at least some tangible surfaces within, outside, or both, of at least a portion of the structure. In non-limiting examples, the map can be digital data describing a three-dimensional array. In non-limiting examples, the map can be configured to identify a location of at least a portion of a tangible surface within a structure, relative to (i) at least a portion of the structure, (ii) at least a portion of another tangible surface within the structure, or (iii) both. In examples, the map can be a three-dimensional map. In some examples the map can be created from digital images, such as digital images captured by the sensor 197. In a non-limiting example, the structure can include at least one room. In non-limiting examples, the structure can be a hospital, a school, an office building, a retail store, a warehouse, a location including a potentially contaminated surface, the like, or a combination thereof.

As illustrated in FIG. 2, at block 210, one or more of the devices described herein can identify a first location of a robot (e.g., the robot 100) in the structure. In an example, the first location can be identified from the digital images.

As illustrated in FIG. 2, at block 215, one or more of the devices described herein can segment (e.g., by a physical processor and using a machine learning-based classifying algorithm) the digital images to identify potentially contaminated surfaces located in the at least the portion of the structure.

The machine learning-based classifying algorithm can be trained with training data including: (i) images of object surfaces known to be potentially contaminated and (ii) respective predictor weights. The respective predictor weights can be: (i) respectively associated with the images of the object surfaces and (i) based on object affordance information identifying respective levels of potential contamination of the object surfaces depicted in the images of the object surfaces known to be potentially contaminated.

In some embodiments, the method 200 can further include initiating training the machine learning-based classifying algorithm with the training data. In some embodiments, the training data can include digital information describing images of object surfaces known to be potentially contaminated in the at least the portion of the structure.

As illustrated in FIG. 2, at block 220, one or more of the devices described herein can create a map of the potentially contaminated surfaces within the structure.

As illustrated in FIG. 2, at block 225, one or more of the devices described herein can calculate a trajectory of movement of at least a portion of the robot to move the at least the portion of the robot to a location of at least a portion of the potentially contaminated surfaces, where the trajectory of movement can be calculated from the map of the at least a portion of the structure, the first location of the robot in the structure, and the map of the potentially contaminated surfaces within the structure.

In some examples, (i) the trajectory of the movement can be configured to move the robot from the first location of the robot in the structure to a second location of the robot in the structure and (ii) the second location of the robot in the structure can be within an effective disinfecting range of a directional decontaminant source relative to at least one potentially contaminated surface in the potentially contaminated surfaces.

In some embodiments, the calculating the trajectory of the movement of the at least the portion of the robot can further include calculating the trajectory of the movement from digital information indicating waypoints along a path to be following by an end-effector of the robot.

As illustrated in FIG. 2, at block 230, one or more of the devices described herein can move the at least the portion of the robot along the trajectory of movement to position the directional decontaminant source adjacent to the location of the at least the portion of the potentially contaminated surfaces.

In some embodiments, the computer-implemented method can further include receiving a user input directing the robot to at least one of: (i) disinfect a specific area in the structure or (ii) perform the initiating creating the map of the at least the portion of the structure at a specific time.

In some embodiments, the computer-implemented method can further include: (i) receiving information indicating present physical contact between a human and the robot and (ii) initiating stopping, responsive to the information indicating present physical contact, the movement by the at least the portion of the robot. In some examples, information indicating present physical contact between a human and the robot can be provided by an electromechanical contact sensor, an electromechanical proximity sensor, a change in current of a moving electromechanical actuator of the robot, a change in current of a motor of the robot, or a combination thereof.

Figure 3:
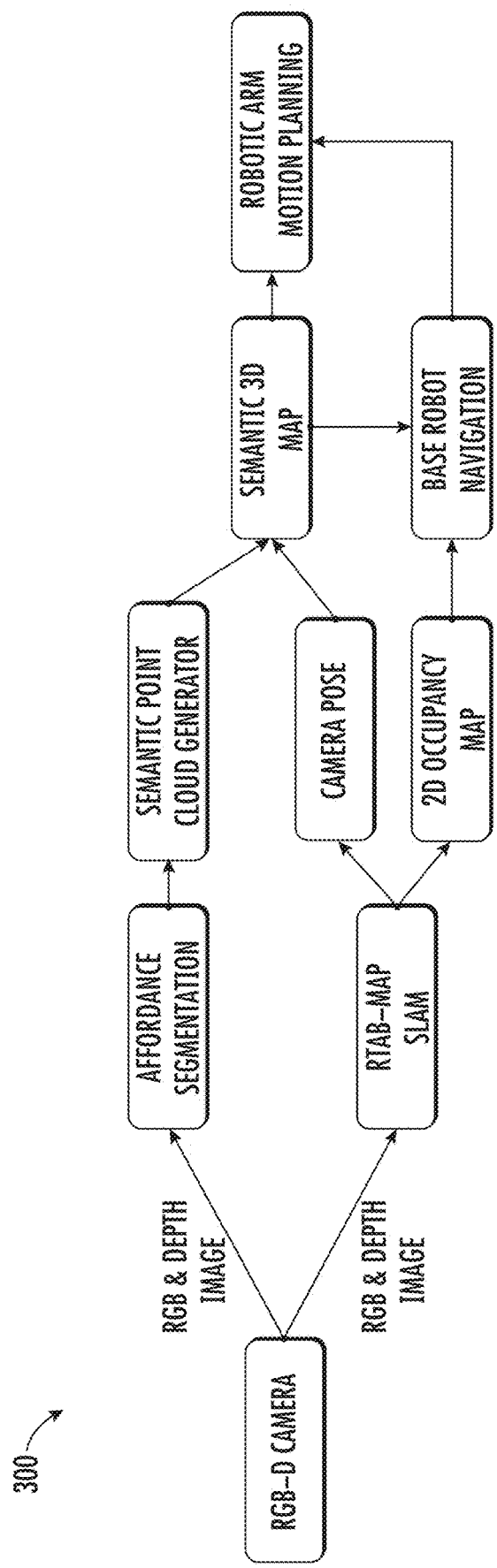
FIG. 3 depicts another block diagram of an example method for environment-adaptive robotic disinfecting.

FIG. 3 depicts an overview of a proposed method 300 that enables intelligent robotic disinfection in built environments. The robot can be equipped with an RGB-D camera for SLAM and perception in built environments. An RTAB-Map can be used to provide pose estimation and generate a two-dimensional occupancy map. A deep learning method can segment object affordance from the RGB-D images and map the segments to areas of potential contaminations in a three-dimensional map. The high-touch areas can be automatically detected and segmented, which may be colonized by a variety of pathogens. The three-dimensional semantic occupancy map and the locations of the areas of potential contamination can be exploited for robot disinfection planning. The robots, with UV lights attached to end-effectors, can navigate to appropriate positions, and can adapt their scanning trajectories to disinfect the objects.

Localization and Mapping Examples

Figure 4:
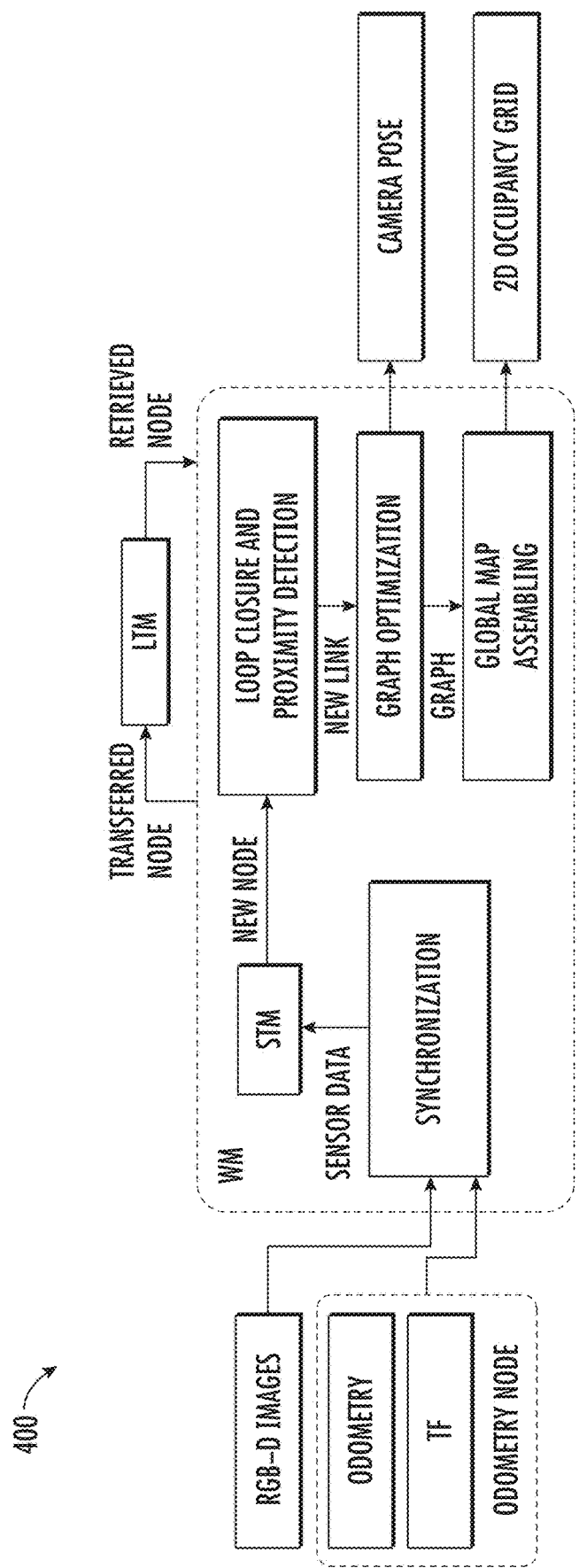
FIG. 4 depicts an example block diagram of a simultaneous localization and mapping (SLAM) framework based on real-time appearance-based mapping (RTAB-Map).

The RTAB-Map SLAM method, a graph-based SLAM technique, can be used to locate the robot and to produce the occupancy map for navigation. FIG. 4 depicts an example RTAB-Map SLAM framework 400. A structure of the map can include nodes and links. Odometry nodes can publish odometry information to estimate robot poses. Visual odometry obtained from ORB-SLAM2 can be used as odometry input in this study, because ORB-SLAM2 can be fast and accurate. A short-time memory (STM) module can be used to create nodes to memorize the odometry and RGB-D images, and to calculate other information such as visual features and local occupancy grids. In order to limit the working memory (WM) size and reduce the time to update the graph, a weighting mechanism can be used to determine which nodes in WM are transferred to long-term memory (LTM). Nodes in the LTM can be brought back to WM when a loop closure is detected. Links can be used to store transformation information between two nodes. The neighbor and loop closure links can be used as constraints for graph optimization and odometry drift reduction. A Bag of Words approach can be used for loop closure detection. The visual features extracted from local feature descriptor such as Oriented FAST and rotated BRIEF (ORB) can be quantized to a vocabulary for fast comparison. The outputs from RTAB-Map can include camera pose and two-dimensional occupancy grid, which can be further used for semantic mapping and robot navigation. The RTABMAP-ROS package can enable seamless integration with autonomous robots for this application. Because the settings of built environments do not change very frequently, maps of the built environments can be first produced and then used to locate and navigate the robots during the cleaning and disinfection process to improve the efficiency and reduce memory use.

Three-Dimensional Segmentation of Areas of Potential Contamination

The areas of potential contamination should be automatically detected and mapped in three-dimensional space to guide robotic disinfection. Particularly, the object surfaces with frequent human contacts can be areas of potential contaminations requiring disinfection. Therefore, those areas should be automatically detected and segmented from the RGB images, and thereafter projected to a three-dimensional semantic map for robot navigations and actions. To this end, a deep learning method is provided based on an object affordance concept and used to segment the areas of potential contamination. It can be necessary to label a surface that has interactions with different parts of human body. For example, a seating surface of a chair has contact with human hip, the backrest has contact with human back, and the armrest has contact with human hand, thus posing different implications for distinction. In a nonlimiting example, five object affordance labels are selected, including walk, grasp, pull, place, and sit, as these activities cover the most common interactions between humans and inanimate objects in built environments. For example, walkable areas indicate the places where the robot can move and conduct floor cleaning. The places where grasping, pulling, and placing occur represent potential high-touch areas that can need to be frequently disinfected.

In a nonlimiting example, training a deep learning method to segment the object surfaces as the areas of potential contamination can include using training datasets (e.g., a ADE20K training data set) and simulated images with appropriate labels. FIGS. 5A-5D depict sample real life images 500 from a training data set.

Figures 5A, 5B, 5C, 5D:
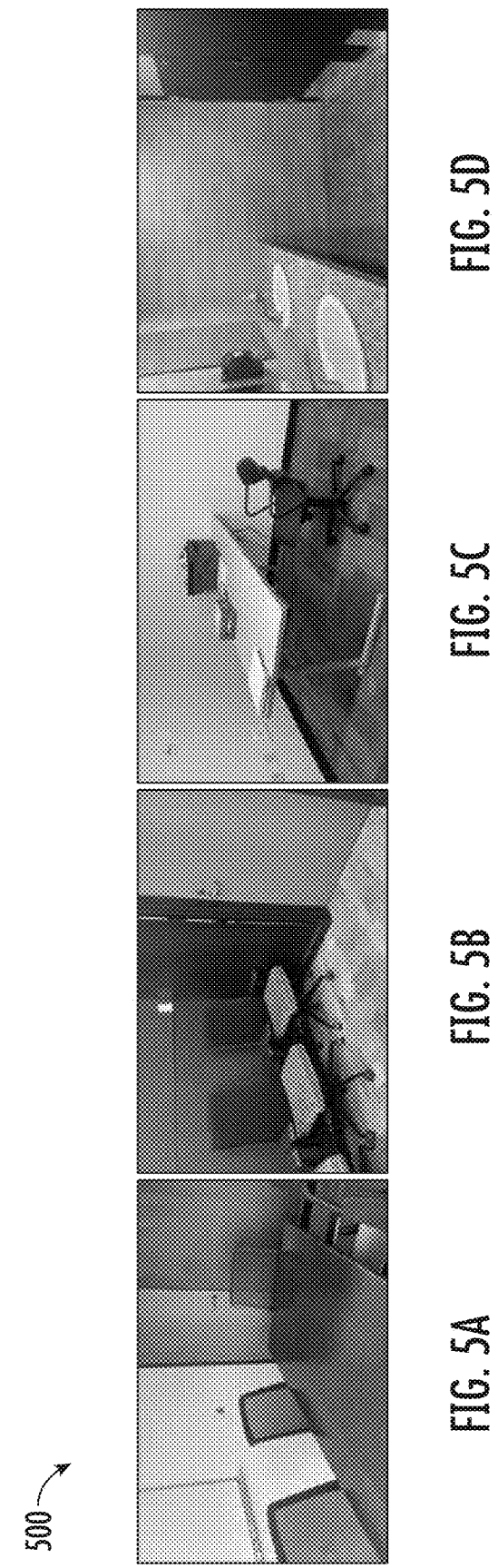
FIGS. 5A-5D depict example training data images of object surfaces known to be potentially contaminated.

FIG. 5A depicts an image of a conference table and chairs on a floor in a structure.

FIG. 5B depicts an image of chairs on a floor of a structure and a door.

FIG. 5C depicts an image of an office in a structure. The office includes a desk, a chair, and a floor of the structure.

FIG. 5D depicts an image of a restroom in a structure. The restroom includes sinks, a countertop, a door, and a floor of the structure.

Figure 6:
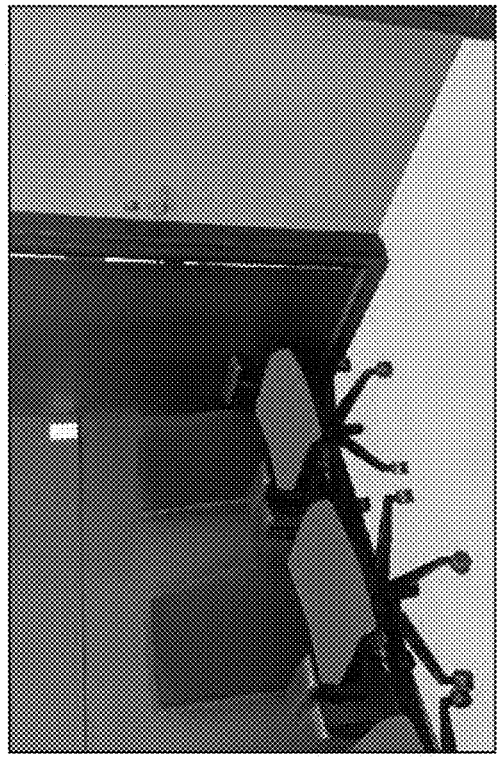
FIG. 6 depicts an example annotated dataset using a transfer table to transform original object labels in a training data set to affordance labels and depicts example annotated images.
Figure 6:

In examples, the training dataset may have labels for objects, parts of the objects, or both. A transfer table can be defined to map object labels to the corresponding five object affordance labels. Table Two presents several nonlimiting examples of a transfer table. Each object or part of the object can be associated with a five-dimensional vector, representing the five object affordance labels. A value of "1" indicates that a specific object affordance is associated with an object or a part of the object, and a value of "0" indicates that a specific object affordance is not associated with an object or a part of the object. For example, "floor" is associated with "walk" affordance, "*/door/knob" is associated with "pull" affordance. If the correspondence between an object and the five affordance labels cannot be established, then the association will not be performed to ensure the reliability of predicting affordance from the trained network. FIG. 6 presents an example of a label transformation 600 from original object labels in a training dataset to affordance labels. Using Table Two, annotated data from the training dataset can be transferred to affordance ground truth data. For instance, a seat base is transferred to sit affordance.

TABLE TWO

Examples of a transfer table

| Affordance | Seat | Bottle | Floor | */door/knob | Countertop | ... |
|---|---|---|---|---|---|---|
| Walk (surfaces a human can walk) | 0 | 0 | 1 | 0 | 0 | ... |
| Grasp (objects that can be grasped and moved by hands) | 0 | 1 | 0 | 0 | 0 | ... |
| Pull (surfaces that can be pulled by hooking up fingers or by a pinch movement) | 0 | 0 | 0 | 1 | 0 | ... |
| Place (elevated surfaces where objects can be placed on) | 0 | 0 | 0 | 0 | 1 | ... |
| Sit (surfaces a human can sit) | 1 | 0 | 0 | 0 | 0 | ... |

Figure 7:
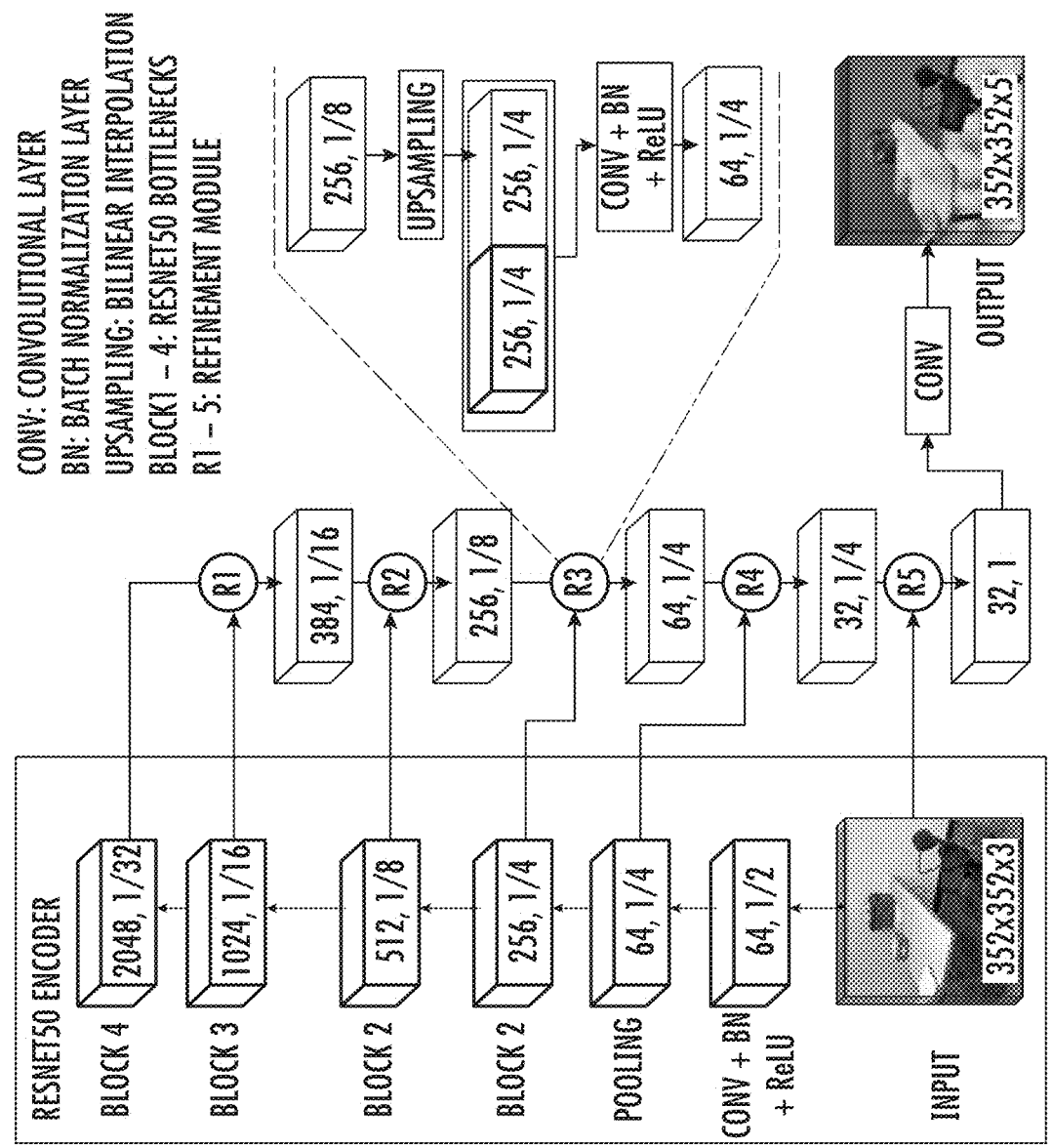
FIG. 7 depicts an example semantic segmentation with a convolutional neural network (CNN) architecture for semantic segmentation (U-NET).

The deep learning method can implement a convolutional neural network (CNN) following the U-Net architecture. An encoder-decoder architecture is efficient for training and implementation when the input and output images are of similar sizes. FIG. 7 depicts an example U-Net architecture implementing semantic segmentation 700. A ResNet50 network can be used as an encoder. The architecture of ResNet50 includes a basic block and a bottleneck block, shown in FIG. 7. The basic block can include convolution, batch normalization, ReLU, and max-pooling layers. An initial 7*7 convolution with a stride of 2 can be first applied, followed by the batch normalization and ReLU activation layer. Thereafter, a max-pooling operation is conducted with a kernel size of 3 and a stride of 2. The two steps can reduce the spatial size, and thus reduce a computation cost and a number of parameters in the deep layers. In the bottleneck, the network can have four connected blocks. As the network progresses from a shallow block to a deep block, the spatial size of the input image reduces to half, and the channel number doubles.

For the decoder network, a refinement module can be used to integrate low-level features and high-level semantic information from encoder network, and thus enhancing mask encoding. First, the refinement module can upsample a feature map size to be the same as that of a skip connection from the encoder network. The bilinear interpolation method can be used to perform upsampling. Then, the skip feature map can be concatenated with the local feature map. Last, convolution and batch normalization with ReLU activation can be performed to compute a feature map of the next layer.

After segmenting the object affordance from the two-dimensional RGB images as the areas of potential contamination, the provided methods can project the two-dimensional labels to a three-dimensional grid map for guiding robot navigation and disinfection. As depth images are registered to the reference frame of RGB images, the first step is to use a classical pinhole camera model to obtain a point cloud of the environment. Given a pixel (x, y) and its depth d, its world coordinate (X, Y, Z) can be computed by Eq. (1), where $f_x$, $f_y$ are the camera focal length in pixel units, ($c_x$, $c_y$) represents the principal point that is usually at the image center.

Figure 8:
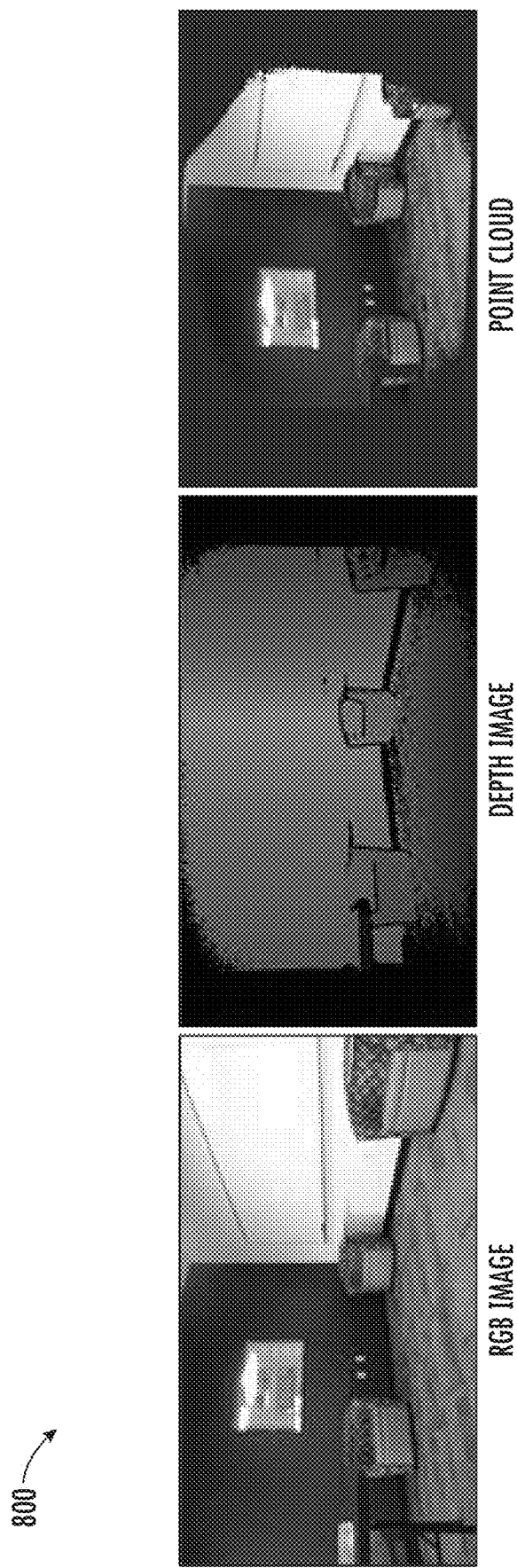
FIG. 8 depicts an example of point cloud generation.

FIG. 8 depicts an example of point cloud generation 800, Including an example of an obtained point cloud. FIG. 8 depicts an RGB image, a depth image, and a point cloud image. Each point can store information of world coordinates, label information, and its highest probability predicted by the network.

$$\begin{bmatrix} X \\ Y \\ Z \end{bmatrix} = \begin{bmatrix} f_x & 0 & c_x \\ 0 & f_y & c_y \\ 0 & 0 & 1 \end{bmatrix}^{-1} \begin{bmatrix} x \\ y \\ d \end{bmatrix} \quad (1)$$

Figure 9:
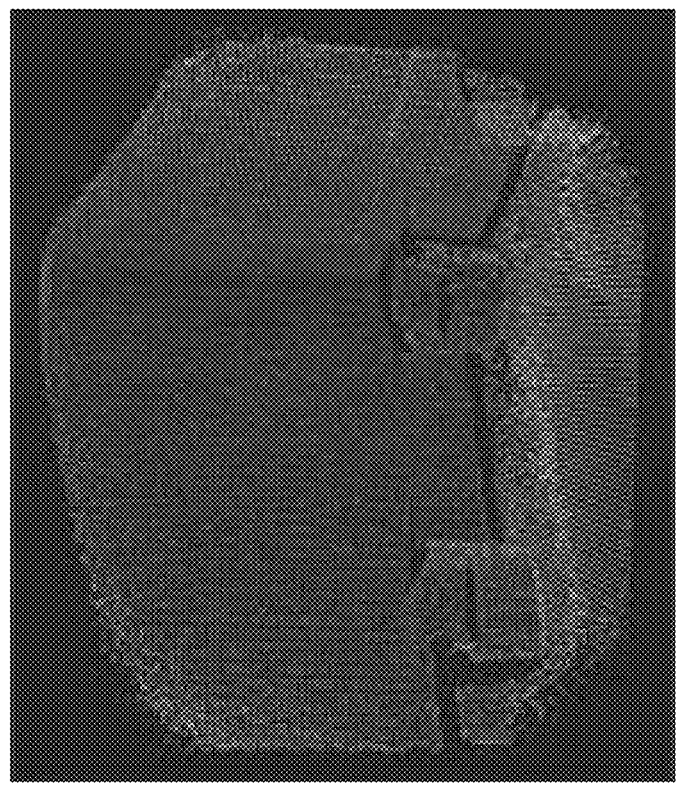
FIG. 9 depicts an example of using a voxel filter for three-dimensional mapping.
Figure 9:
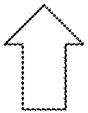
Figure 9:
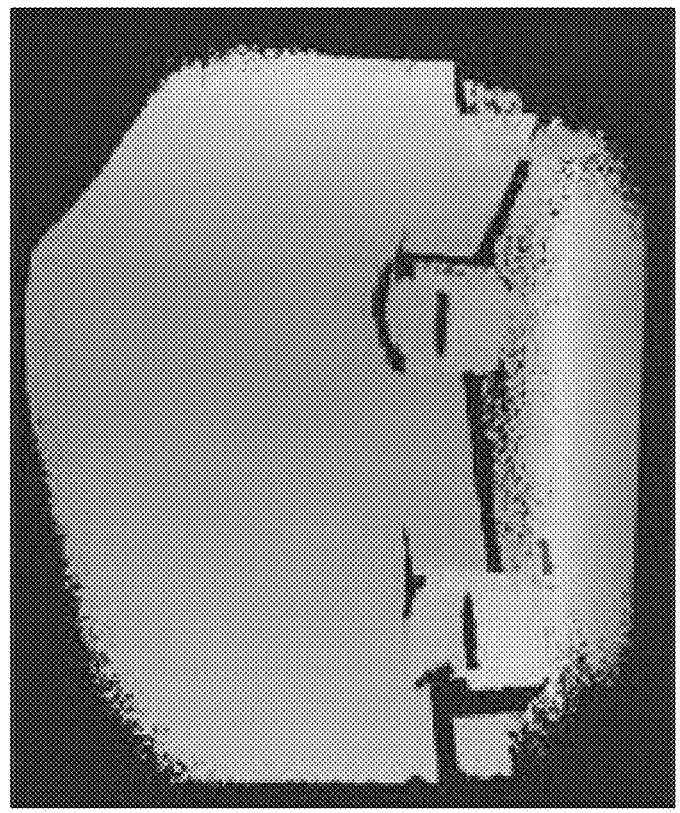
Figure 11:
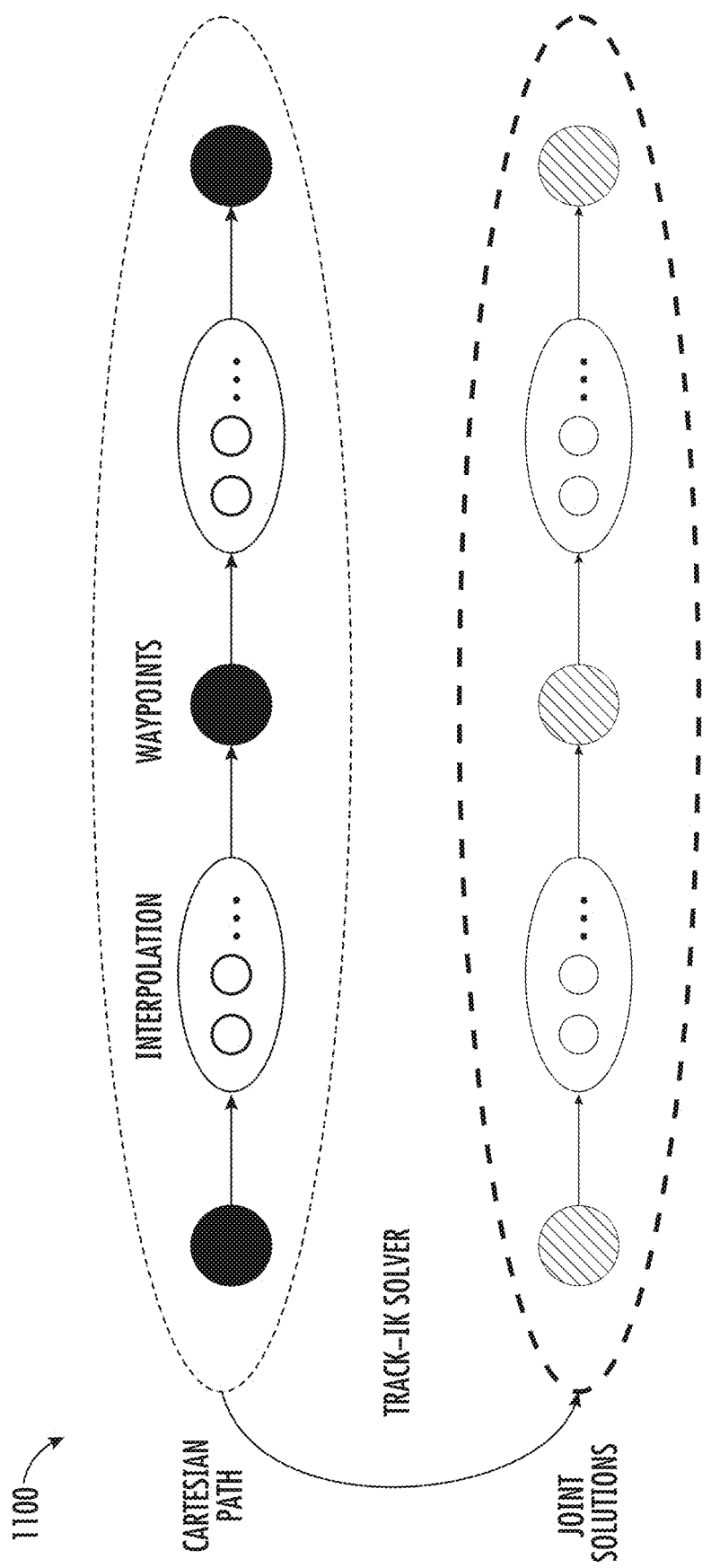
FIG. 11 depicts an example of a flowchart that generates a trajectory from waypoints.

Next, an octomap library can be applied to generate a three-dimensional occupancy grid map, using the obtained point cloud as input. A voxel filter can be used to reduce the size of the point cloud to accelerate the mapping process. In each voxel space, only one point may be stored as one point is adequate to update an octree node. The voxel filter resolution can be set to the same resolution as that of the occupancy map. The resolution of the occupancy map can be set as 4 cm, which can provide adequate details in indoor environments while maintaining processing efficiency. FIG. 9 presents a nonlimiting example of a three-dimensional point cloud filtering using a voxel filter 900. The image size can be 960×540 and 518,400 points can be generated for each frame. After using the voxel filter, the number of points can reduce to 23,009 for the frame shown in FIG. 9. The number of filtered points can vary from frames due to noises in sensory data.

Since the camera is constantly moving, semantic information may continuously update. For instance, a small object may not be accurately segmented when the camera's view angle is not at a favorable position. Hence, semantic information at the pixel level from different frames can be fused to deal with this situation, such as by implementing the example pseudocode for semantic fusion of two different frames 1000 depicted in FIG. 10. If two affordances are the same, the affordance can be kept, and the probability becomes the average of the two affordances. Otherwise, the affordance with higher confidence can be kept and the probability can be decreased to 0.9 of its original probability. This process can enable the occupancy map to update the semantic information with a new prediction of higher confidence. After the above steps, the areas of potential contamination are predicted and projected to the three-dimensional occupancy map, which can further guide the robotic disinfection.

Motion Planning for Robotic Disinfection

After mapping the areas of potential contamination, a following step is generating robot motions to scan the areas of potential contamination with UV light for disinfection. In a nonlimiting example, the robot can have a three degree of freedom base and can have a six degree of freedom manipulator. The robot may need to move to the object needing disinfection. A hierarchical planning approach can be used, which can include global path planning, local path planning, or both. Global path planning provides an optimal path from a start to a goal location. Local path planning can output a series of velocity commands for the robot. The "A*" algorithm can be used to find a globally optimal path for the robot. The heuristic function h(n) can be used to guide the trajectory search toward the goal position. The "A*" algorithm can find the shortest path very efficiently. Examples, the Manhattan distance can be used as the heuristic function that is defined in Eq. (2). This equation can be used to calculate a Manhattan distance from any node (n ($x_n$, $y_n$)), to the goal (g ($x_g$, $y_g$)) in the graph.

$$h(x_n, y_n) = |x_n - x_a| + |y_n - y_a| \quad (2)$$

The cost function is given in Eq. (3), where g(n) is the cost from starting point to node n, f(n) is the total cost. The objective can be to minimize the total cost.

$$f(n) = g(n) + h(n) \quad (3)$$

Given a global path to follow, the local planner can produce velocity commands for the robot. The Dynamic Window Approach (DWA) algorithm can serve as the local planner. The algorithm can sample velocities in the robot's control space discretely within a given time window. The samples that intersect with obstacles can be recognized and eliminated. An optimal pair of (v, w) for the robot can be determined by finding the minimum cost defined in Eq. (4), which can be dependent on proximity to the global path, proximity to the goal, and proximity to obstacles.

$$\text{cost} = \alpha f_a(v, w) + \beta f_d(v, w) + \gamma f_c(v, w) \quad (4)$$

where $f_a(v, w)$ represents the distance between global path and the endpoint of the trajectory, $f_d(v, w)$ is the distance to the goal from the endpoint of the trajectory, $f_c(v, w)$ is the grid cell costs along the trajectory, α is the weight for how much the controller should stay close to the global path, β is the weight for how much the robot should attempt to reach the goal, and γ is the weight for how much the robot should attempt to avoid obstacles.

After moving to the vicinity of the objects, the scanning-based disinfection can be conducted. Because the ultraviolet light has been demonstrated to effectively reduce the bioburden of epidemiologically relevant pathogens, an ultraviolet disinfection device can be integrated into a mobile manipulator of the robot as an end-effector. Continuous low doses of ultraviolet light can kill pathogens on various surfaces of the objects without harming human tissues. Human interventions can also be incorporated to guide the robot disinfection. For example, humans can issue commands to a robot to disinfect a particular area or object or schedule a fleet of robots to disinfect large facilities such as hospitals, schools, airports, etc. In addition, the human user could further adjust the autonomy or can force any decision of the robot regardless of what and how the onboard operation progresses. For instance, the user could stop the robot immediately in any unexpected safety-critical situations.

A list of waypoints can be used as inputs to generate a trajectory for robotic disinfection.

Waypoints are defined as individual points along the path followed by the end-effector. There can be four steps to generate a trajectory from waypoints (see FIG. 11, which depicts an example of a flowchart that generates a trajectory from waypoints 1100). First, sampling points can be linearly interpolated between the first waypoint and the second waypoint. In an example, 1 cm resolution can be used to interpolate the points. The number of points between the two waypoints is the distance divided by the resolution. Second, TRAC-IK algorithm can be used as an inverse kinematics (IK) solver to calculate joint solutions. This algorithm is a numerical IK solver that combines both pseudoinverse Jacobian and Sequential Quadratic Programming-based nonlinear optimization solvers. The solver will stop and return the best solution once either of the two solvers finishes with a solution. Third, taking the current position as the starting position and next waypoint as the goal, the first and second steps can be repeated until all the waypoints are traversed. Finally, all the joint solutions are connected to generate a trajectory that can include velocity, acceleration, duration, or combination thereof.

Figure 12:
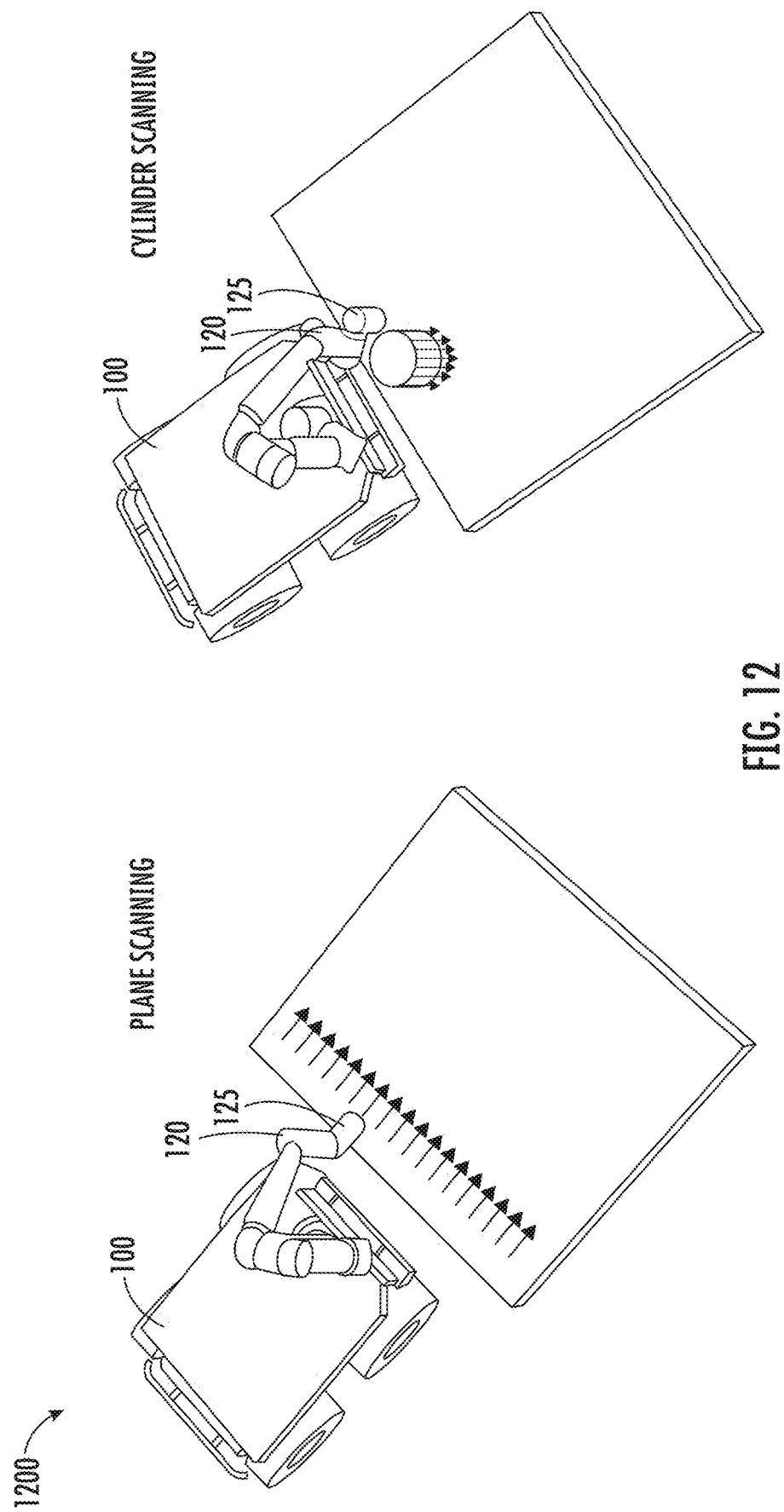
FIG. 12 depicts an example of plain scanning and cylinder scanning zones. The arrows represent example waypoints and their corresponding poses along a trajectory.

To make the disinfection process more efficient, the robotic arm can be preprogrammed to adapt to objects with various geometries. FIG. 12 depicts an example of plain scanning and cylinder scanning zones 1200. As shown in FIG. 12, a plane scanning zone and a cylinder scanning zone can be developed to generate scanning trajectories for different objects. In FIG. 12, the arrows represent waypoints and corresponding poses along a trajectory. Plane-scanning is suitable for objects that have plane surfaces, such as an office desk, a keyboard, a push bar of drinking fountain, etc. Cylinder-scanning is suitable for objects that have large curvature such as a kettle. The two types of scanning zones can account for a variety of objects that are commonly seen in the built environments. The size of the scanning zone can adapt to the segmented areas of potential contamination. Based on the three-dimensional segments, a distance away from the surface can be maintained to generate the scanning zones and trajectories.

Example Experimental Results

Both simulations and physical experiments were conducted to validate the proposed methods. Segmentation and three-dimensional mapping of potential areas of contamination were validated in indoor environments, including a dining structure, a conference structure, and a rest structure in a university campus building. Motion planning for robotic disinfection was validated using a robot simulation platform and an AUBO-i5 robotic arm.

Example Segmentation and Mapping Evaluation

In an example, the ADE20K training dataset and simulated dataset were used to evaluate the performance of the network. The ADE20K dataset includes a total of 22,210 images with 20,210 training images and 2,000 validation images. The simulated dataset includes 2,530 synthetic images with 2,280 training images and 250 testing images. Hence, a total number of 22,490 images including both real and simulated images were used for training. The real and simulated images were first merged and then randomly mixed. Each mini batch for training can have samples from both datasets. In addition, a data augmentation technique is used to increase its volume and variability of the training dataset. Training samples were augmented by cropping multiple image patches based on image quality and varying color and contrast of images to improve the capability and generalization of the trained model. Online augmentation method is used in this example due to two reasons.

First, as the model observes more samples in the training process, the model trained with online data augmentation can generalize better than the model trained with offline data augmentation. Second, online augmentation does not need to store a large amount of augmented data in local disk. The validation set includes 1,000 real images and 120 simulated images that are randomly split from the training dataset. The performance of the network was evaluated on 2,000 real images and 250 simulated images.

To evaluate the performance of affordance segmentation, metrics including the intersection over union (IoU), dice coefficient (DSC), and average precision (AP) were used to evaluate the network performance in the performance of semantic segmentation. The IoU is the area of overlap between the predicted segmentation and the ground truth divided by the area of union between the predicted segmentation and the ground truth. The maximum IoU value is 1 representing perfect segmentation. The IoU metric is defined in Eq. (5), where $Y_{ai}$, is the ground truth for affordance a at pixel i ∈ I, $\hat{Y}_{ai}$ represents predicted affordance. The binarized prediction of the network is used to compute the IoU. The threshold values 0.2 and 0.5 are used in the experiment.

$$IoU_a = \frac{\sum_{i \in I}(Y_{ai} = 1 \cap \hat{Y}_{ai} = 1)}{\sum_{i \in I}(Y_{ai} = 1 \cup \hat{Y}_{ai} = 1)} \qquad (5)$$

$$\hat{Y}_{ai} = \begin{cases} 1 & \text{if } p > \text{threshold} \\ 0 & \text{else} \end{cases}$$

The DSC is similar to the IoU, which is another measure of overlap between prediction and ground truth. This measure ranges from 0 to 1, where a DSC of 1 denotes perfect and complete overlap. The DSC is defined in Eq. (6).

$$DSC_a = \frac{\sum_{i \in I} 2 \times (Y_{ai} = 1 \cap \hat{Y}_{ai} = 1)}{\sum_{i \in I}(Y_{ai} = 1) + (\hat{Y}_{ai} = 1)} \qquad (6)$$

The AP metric summarizes a precision-recall curve as the weighted mean of precisions achieved at each threshold. AP is not dependent on a single threshold value since it averages over multiple levels. The AP is defined in Eq. (7), where $P_n$ and $R_n$ are the precision and recall at the nth threshold, and $P_n$ is defined as precision at cut-off n in the list.

$$AP = \sum_n (R_n - R_{n-1}) P_n \quad (7)$$

In this experimental example, the models were trained on a workstation running Ubuntu 16.04 with Dual Intel® Xeon® Processor E5-2620 v4, 64 GB RAM, and Dual NVIDIA® Quadro P5000® with a pytorch backend. The network was trained using RMSProp optimizer with a learning rate of 0.0001 and batch size of 16. The ResNet50 encoder was initialized with weights pretrained on ImageNet. The pretrained weight was further trained on the dataset without freezing any weights. The early stopping technique was adopted to prevent overfitting. Specifically, the network is trained on the training set, and if the loss on the evaluation set does not decrease for 20 epochs, the training process will stop and the best model observed on the evaluation set will be saved. The performance of the network is evaluated on the testing dataset.

Figure 13:
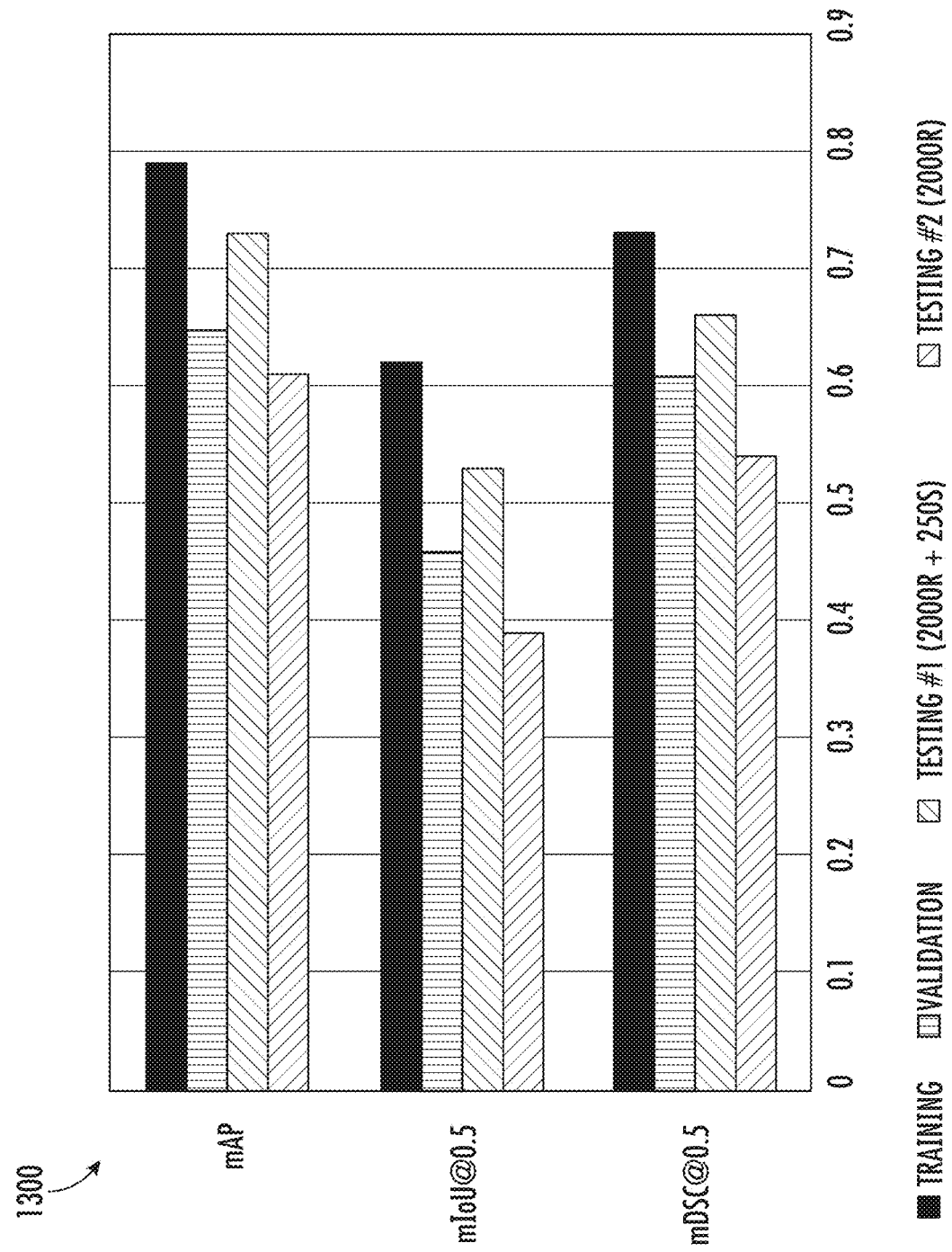
FIG. 13 depicts example performance results of network on a training set validation set and two testing sets.

FIG. 13 depicts example performance results 1300 of the affordance segmentation on a training set validation set and two testing sets. Specifically, FIG. 13 depicts performance of a network on the training set, the validation set, and two testing sets. Testing #1 includes of 2000 real images and 250 simulated images and testing #2 includes 2000 real images. mAP, mIoU, and mDSC are the average of AP, IoU, and DSC over all classes. The training set achieved the highest mAP, mIoU, and mDSC since the model is optimized using this set. The testing set #1 achieved the second-highest scores, and the difference of all the three metrics between the training set and testing set #1 is less than 0.1. However, testing set #2 achieved the smallest scores among the four datasets. This is because the training set contains both real and simulated images, while testing set #2 only contains real images. Synthetic images cannot reproduce richness and noise in the real ones, which may lead to the network trained on synthetic images performs undesirable on real images. Therefore, the network trained on both simulated and real images have a better performance on a testing set combines both samples.

Table Three presents the network performance for individual affordance on testing set #2. The results show a strong variation in performance for different affordances. For instance, affordance walk achieves the highest IoU and AP scores, which is attributed to a relatively large sample size compared to other affordances such as grasp and pull. In addition, walking surface often covers large areas in the scene. Pull has the lowest prediction accuracy among the five affordances. The pull affordance represents objects that can be pulled such as doorknob and cabinet handle. These objects are relatively small and have a small sample size in the dataset. The walk, grasp, place, and sit affordances achieved DSC and AP scores higher than 0.5, indicating the usability of the proposed method in built environments.

TABLE THREE

| Performance for individual affordance on testing set #2 | | | | | |
|---|---|---|---|---|---|
| Affordance | DSC@0.2 | DSC@0.5 | IoU@0.2 | IoU@0.5 | AP |
| Walk | 0.84 | 0.87 | 0.72 | 0.77 | 0.94 |
| Grasp | 0.51 | 0.51 | 0.31 | 0.30 | 0.50 |
| Pull | 0.36 | 0.17 | 0.23 | 0.10 | 0.32 |
| Place | 0.57 | 0.56 | 0.38 | 0.37 | 0.62 |
| Sit | 0.64 | 0.60 | 0.47 | 0.42 | 0.67 |

A multi-scale CNN can segment affordance in RGB images. The proposed network achieved 0.76 and 0.42 for IoU scores for walk and sit affordances at the threshold 0.5. The proposed network achieved AP scores 0.67, 0.50, 0.32, 0.62, and 0.94 for sit, grasp, pull, place, and walk affordances on the same test set.

Figure 14:
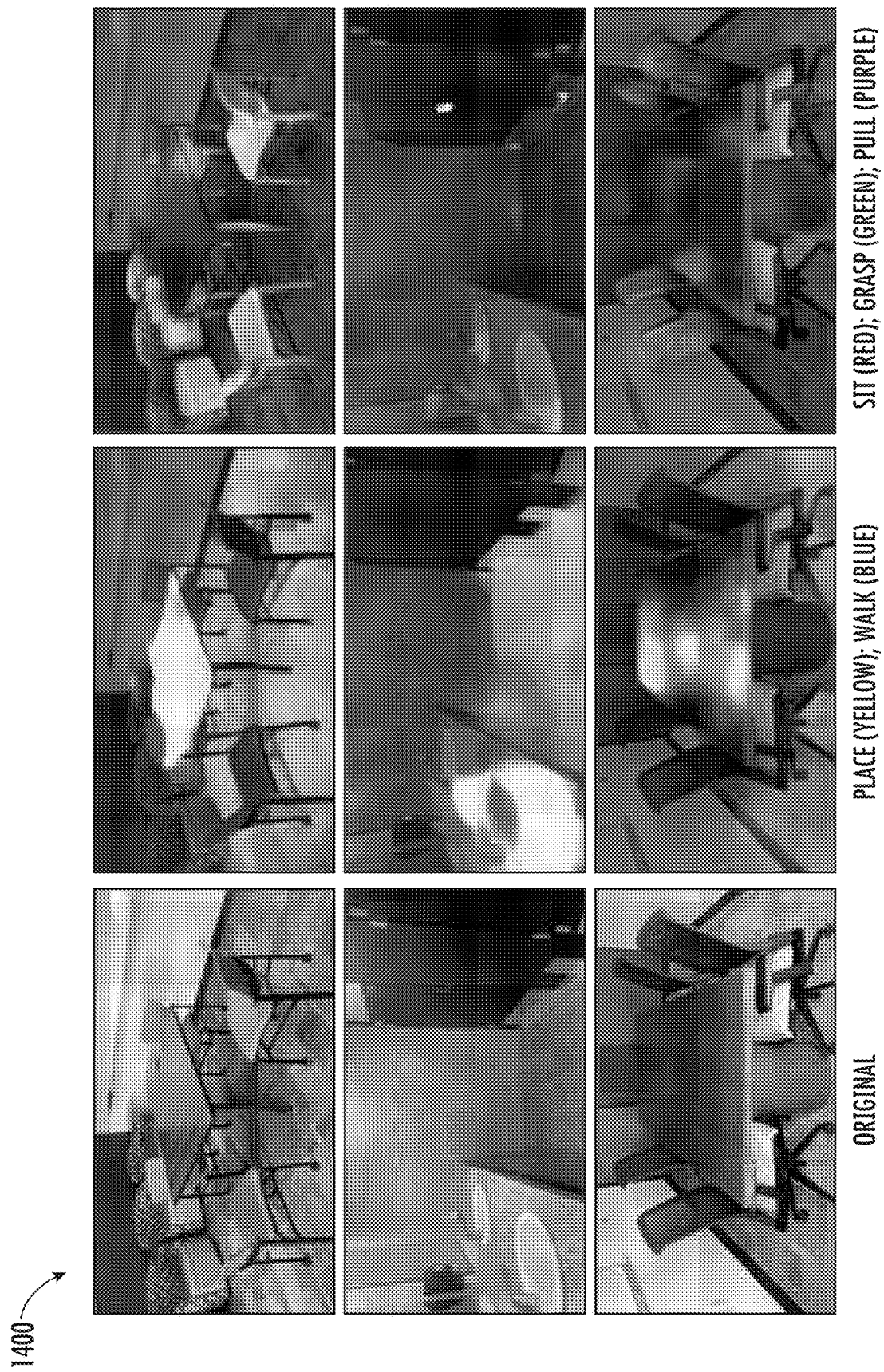
FIG. 14 depicts example results of affordance segmentation.

A Kinect sensor can be used to perform RTAB-Map SLAM and generate the semantic three-dimensional occupancy map using the network. The frame size provided by the Kinect is 960*540 pixels. FIG. 14 shows results of affordance segmentation 1400 of images captured in a building. Walk, Grasp, Pull, Place, and Sit affordances are depicted in FIG. 14.

Figure 15:
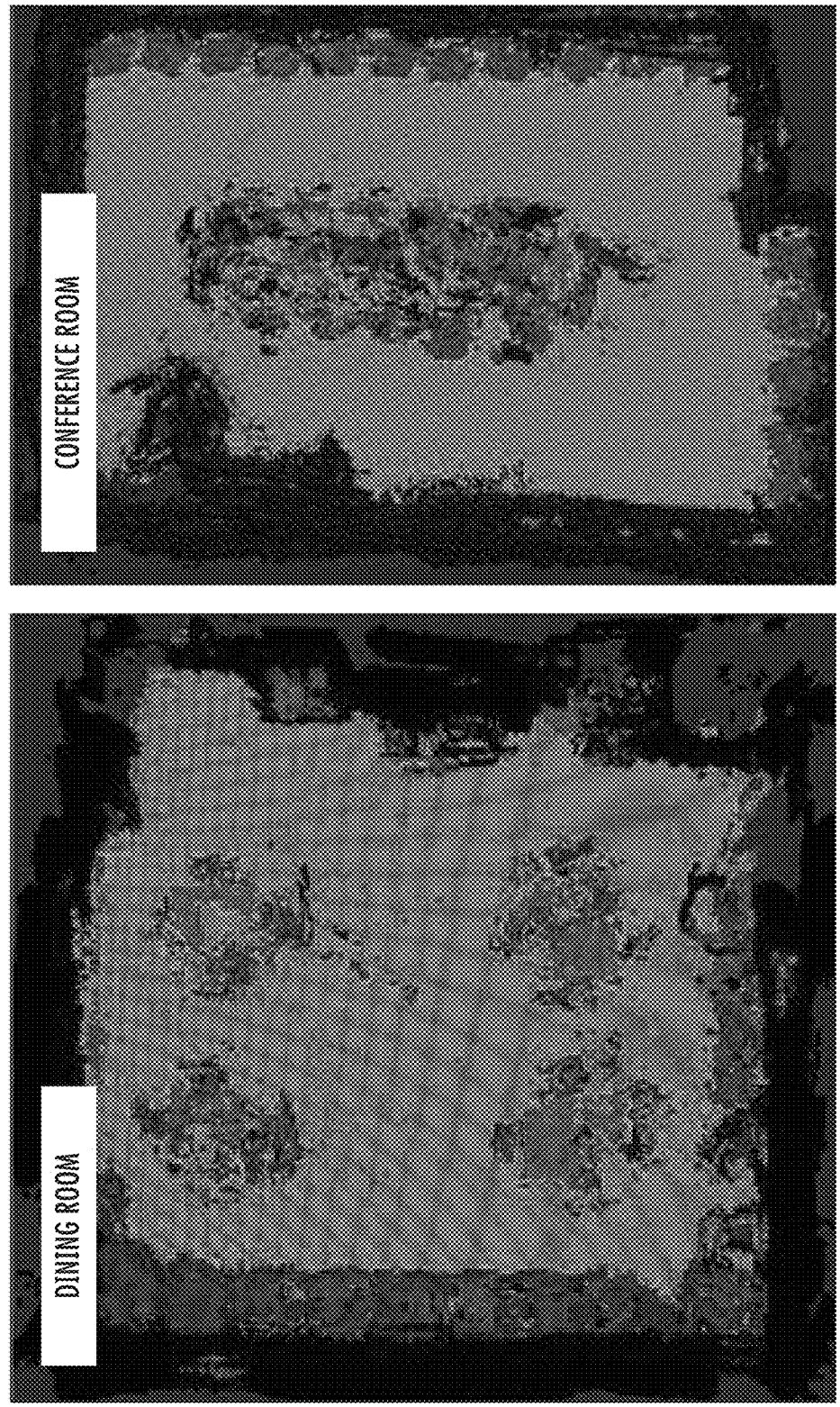
FIG. 15 depicts example results of three-dimensional semantic reconstruction.

FIG. 15 presents results of three-dimensional semantic occupancy mapping 1500. Images were obtained to perform RTAB-Map SLAM to obtain camera poses. Thereafter, semantic reconstruction was conducted using recorded video and camera trajectory. At a resolution of 4 cm, the indoor scene can be properly reconstructed. The results indicate that the proposed method can successfully segment affordances. The walk, place, sit, and grasp affordances are reasonably segmented. In FIG. 15, image (a), a small tablet arm of sofa on the left side is correctly segmented as place affordance. However, small objects like doorknob are not correctly recognized in the semantic map. In addition, a part of the table surface is wrongly identified as walk affordance. This is possibly due to the small size of the training data. The occupancy map can be continuously updated during the robot disinfection action to address the incorrect segmentation.

Processing Times

The processing time for each step was assessed in these experiments. Table Four presents the average time spent on each processing stage. The occupancy map resolution is set as 4 cm. As shown in the table, the processing time of the entire system is about 308.0 ms and 249.8 ms for image size 960×540 and 512×424, respectively. The octomap update is the most time-consuming step in the system, since the octomap update requires raycasting to update occupancy map. The raycasting is used to clear all the voxels along the line between the origin and end point. The SLAM method achieves a high frame rate to track the camera in real time. Semantic segmentation and semantic point cloud generation are also run at a very high frame rate. The processing time of the algorithm is 308.0 ms for a high-resolution image streaming, which can be adapted to most indoor online applications.

TABLE FOUR

| Average processing time for each step (Process with * and process with ** executed at the same time) | | |
|---|---|---|
| | Consumed time | |
| Step | 960 × 540 | 512 × 424 |
| SLAM * | 50.2 ms | 35.4 ms |
| Semantic segmentation ** | 25.1 ms | 20.4 ms |

TABLE FOUR-continued

Average processing time for each step (Process with
* and process with ** executed at the same time)

| | Consumed time | |
|---|---|---|
| Step | 960 × 540 | 512 × 424 |
| Semantic point cloud generation ** | 28.3 ms | 13.7 ms |
| Octomap update (resolution 4 cm) ** | 254.6 ms | 215.7 ms |
| Total | 308.0 ms | 249.8 ms |

Figure 16:
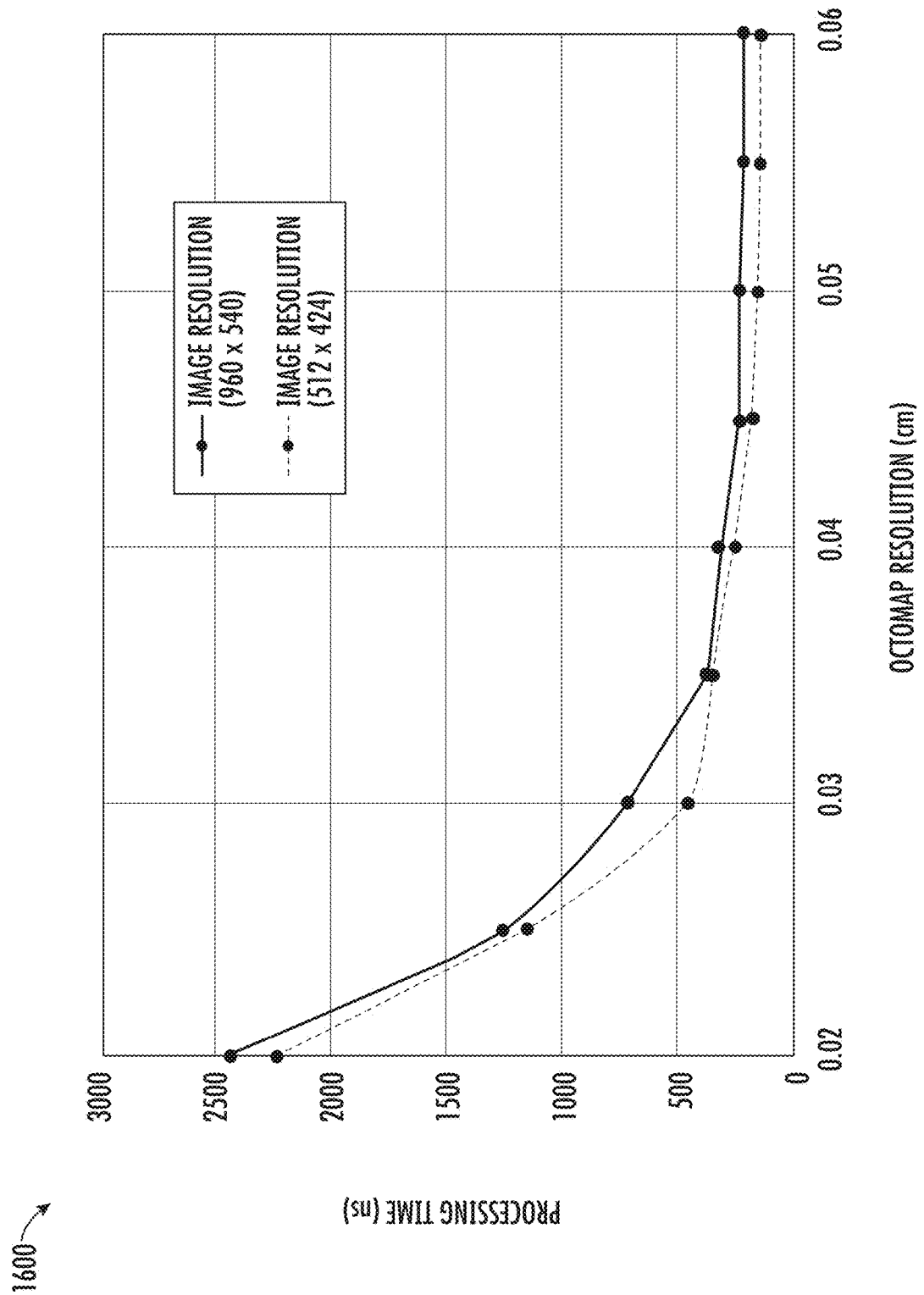
FIG. 16 depicts an example of influence of image size and occupancy map resolution and processing time.

Moreover, the occupancy map resolution can significantly impact the processing time. FIG. 16 presents a relationship 1600 between processing time and occupancy map resolution for images having size 960×540 and 512×424. The result indicates the processing time significantly decreases with decreasing map resolution. In addition, processing time increases as the image size increases under different occupancy map resolutions. When the resolution is 0.06 cm, the processing time can reduce to 206.5 ms and 134.2 ms for image size 960*540 and 512*524, respectively. However, a lower resolution may not capture detailed information, especially for small objects.

Implementation Results

Physical and simulated experiments were performed to test the scanning-based disinfection. A Husky UR5 mobile manipulation robot is simulated in a gazebo. Husky is a mobile robot that can navigate in the ground plane. The UR5 robotic arm can generate a designed path to scan the areas of contamination using ultraviolet light. The distribution of ROS is Kinetic, and the version of Gazebo is 7.16.0. The three-dimensional occupancy map collected in the built environment was loaded into the simulation platform to test robot navigation. Table Five shows the performance of path planning of the robot. The average computing time for 20 simulation experiments is low, and generated paths can successfully avoid collision with obstacles. The results demonstrate the efficiency and effectiveness of the robot path planning method.

Figure 17:
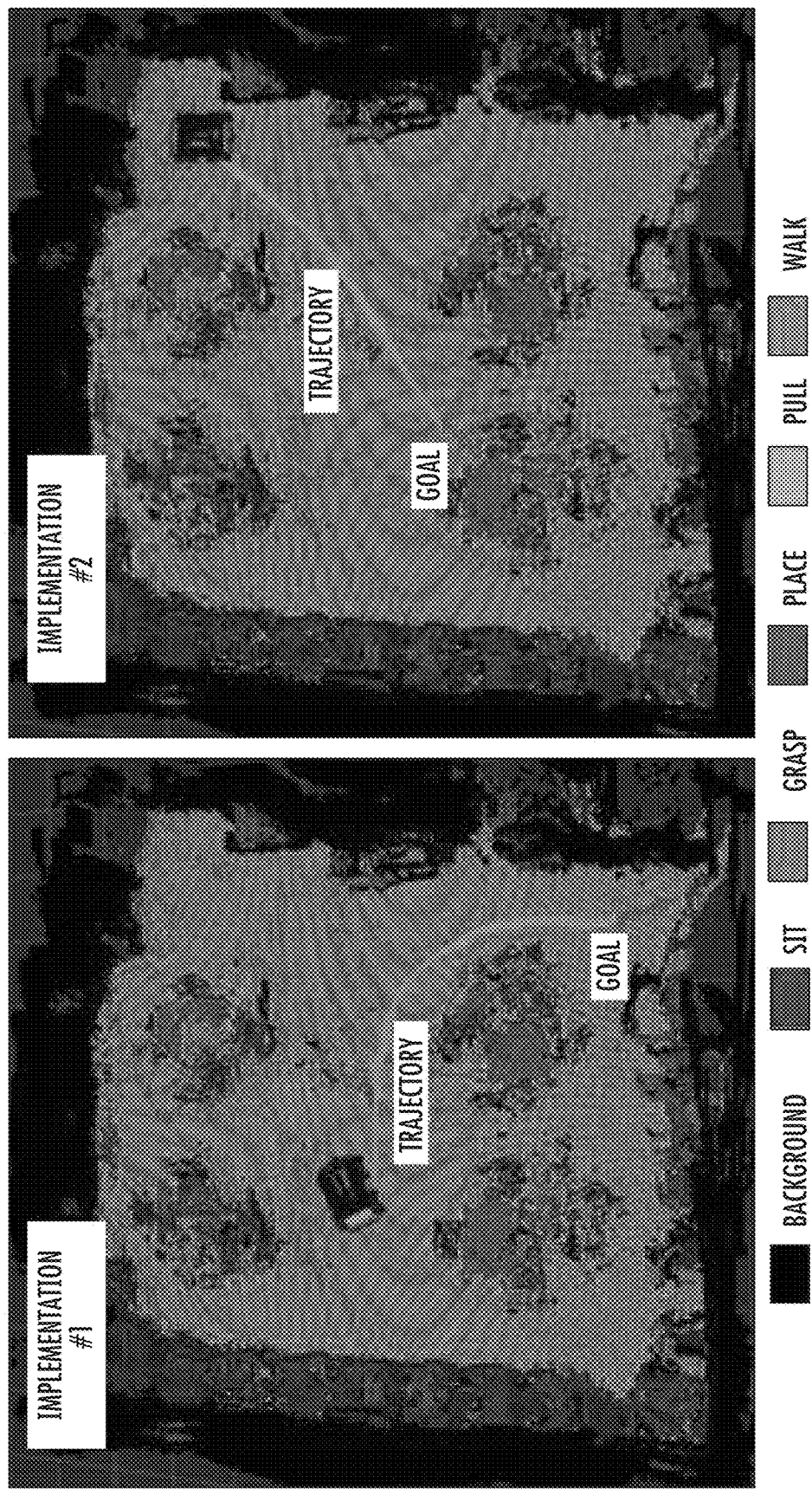
FIG. 17 depicts an example implementation of robot navigation. The arrow is an example pose of a robot moving toward goal point.

FIG. 17 presents two nonlimiting representative examples of path planning 1700 (e.g., robot navigation) of the robot 100, where the arrow is an example pose of moving toward a goal point. Implementing these paths, the robot 100 can move to a proximity of objects needing disinfection.

TABLE FIVE

Performance of base robot path planning

| Simulation case | Computing time (second) | | | Number of cases without collision |
|---|---|---|---|---|
| | Average | Minimum | Maximum | |
| 20 | 0.231 | 0.2 | 0.375 | 20 |

Figure 18:
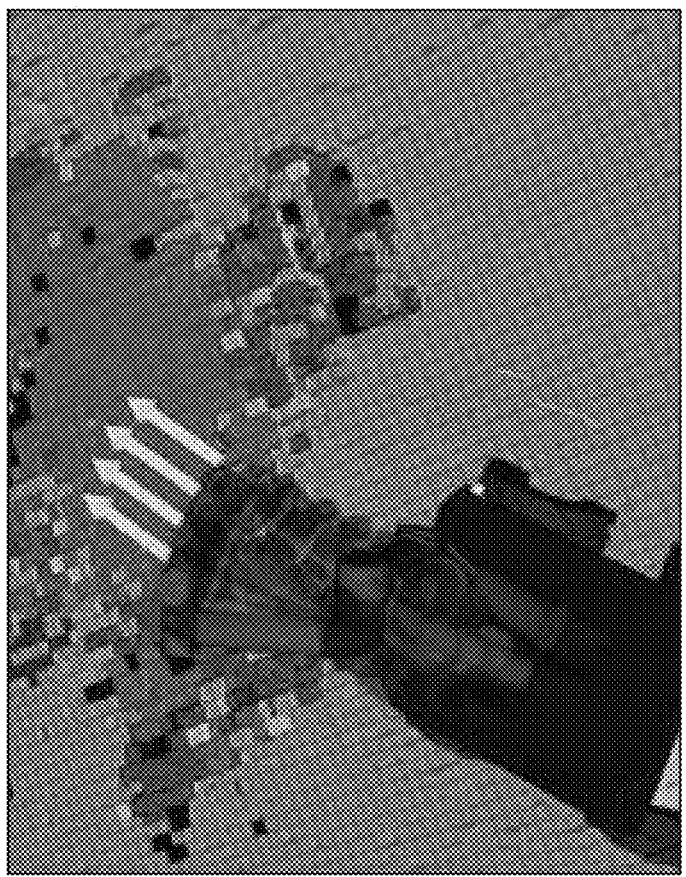
FIG. 18 depicts example results of robotic arm motion planning. The arrows represent example waypoints and they corresponding example pose along an example trajectory.
Figure 18:

After navigating to the areas of potential contamination, a trajectory will be generated to perform disinfection. FIG. 18 presents two examples of results of robotic arm motion planning for robotic disinfection 1800, where a table surface and a sofa seat surface were disinfected with plane scanning. The arrows represent waypoints and their corresponding pose along the respective trajectories. The generated robotic arm trajectories can avoid collisions with objects by using the semantic occupancy map. The execution times in these experimental examples are 2.89s and 4.37s for the sofa seat and part of tabletop, respectively. Additional scanning can be performed to ensure adequate exposure of UV light to eradicate pathogens. The results demonstrate the affirmative feasibility of using robots to conduct disinfection.

Figure 19:
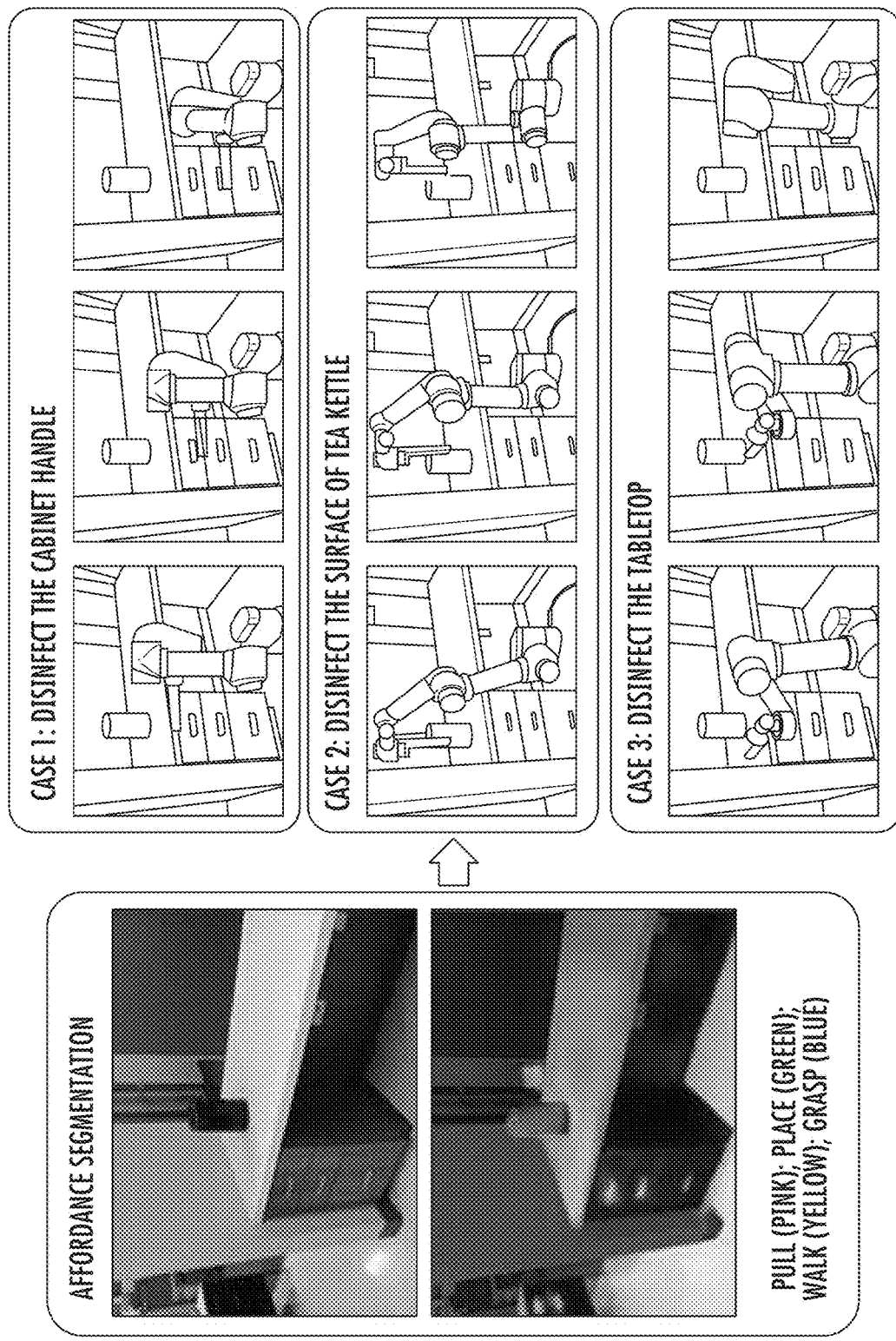
FIG. 19 depicts example results of robotic disinfection based on an affordance map.

In addition, a physical experiment was conducted using an AUBO-i5 robotic arm with an ultraviolet light attached as the robot's end effector. The decontaminant source can automatically turn on when the decontaminant source is close to the object surface requiring disinfection and can shut off when moving away from the object surface requiring disinfection. FIG. 19 depicts example results of robotic disinfection based on affordance map 1900. As shown in FIG. 19, objects are correctly segmented to their corresponding affordances. The cabinet handle, the outside surface of tea kettle, and the table surface are segmented as pull, grasp, and place, respectively. For the cabinet handle and the table surface, plane scanning by the decontaminant source is used to conduct disinfection. The outside surface of tea kettle is disinfected with cylinder scanning by the decontaminant source. The segmentation and mapping of areas of potential contamination provided guidance for robot disinfection in the physical experiments, thus demonstrating the efficacy of the provided apparatus and methods.

As used hereby, the term "example" means "serving as an example, instance, or illustration". Any example described as an "example" is not necessarily to be construed as preferred or advantageous over other examples. Likewise, the term "examples" does not require all examples include the discussed feature, advantage, or mode of operation. Use of the terms "in one example," "an example," "in one feature," and/or "a feature" in this specification does not necessarily refer to the same feature and/or example. Furthermore, a particular feature and/or structure can be combined with one or more other features and/or structures. Moreover, at least a portion of the apparatus described hereby can be configured to perform at least a portion of a method described hereby.

It should be noted the terms "connected," "coupled," and any variant thereof, mean any connection or coupling between elements, either direct or indirect, and can encompass a presence of an intermediate element between two elements which are "connected" or "coupled" together via the intermediate element. Coupling and connection between the elements can be physical, logical, or a combination thereof. Elements can be "connected" or "coupled" together, for example, by using one or more wires, cables, printed electrical connections, electromagnetic energy, and the like. The electromagnetic energy can have a wavelength at a radio frequency, a microwave frequency, a visible optical frequency, an invisible optical frequency, and the like, as practicable. These are several non-limiting and non-exhaustive examples.

The term "signal" can include any signal such as a data signal, an audio signal, a video signal, a multimedia signal, an analog signal, a digital signal, and the like. Information and signals described hereby can be represented using any of a variety of different technologies and techniques. For example, data, an instruction, a process step, a process block, a command, information, a signal, a bit, a symbol, and the like which are referred to hereby can be represented by a voltage, a current, an electromagnetic wave, a magnetic field, a magnetic particle, an optical field, an optical particle, and/or any practical combination thereof, depending at least in part on the particular application, at least in part on the desired design, at least in part on the corresponding technology, and/or at least in part on like factors.

A reference using a designation such as "first," "second," and so forth does not limit either the quantity or the order of those elements. Rather, these designations are used as a convenient method of distinguishing between two or more elements or instances of an element. Thus, a reference to first and second elements does not mean only two elements can be employed, or the first element must necessarily precede the second element. Also, unless stated otherwise, a set of elements can comprise one or more elements. In addition, terminology of the form "at least one of: A, B, or C" or "one or more of A, B, or C" or "at least one of the group consisting of A, B, and C" used in the description or the claims can be interpreted as "A or B or C or any combination of these elements". For example, this terminology can include A, or B, or C, or A and B, or A and C, or A and B and C, or 2A, or 2B, or 2C, and so on.

The terminology used hereby is for the purpose of describing particular examples only and is not intended to be limiting. As used hereby, the singular forms "a," "an," and "the" include the plural forms as well, unless the context clearly indicates otherwise. In other words, the singular portends the plural, where practicable. Further, the terms "comprises," "comprising," "includes," and "including," specify a presence of a feature, an integer, a step, a block, an operation, an element, a component, and the like, but do not necessarily preclude a presence or an addition of another feature, integer, step, block, operation, element, component, and the like.

Those of skill in the art will appreciate the example logical blocks, elements, modules, circuits, and steps described in the examples disclosed hereby can be implemented individually and/or collectively, as electronic hardware, computer software, or combinations of both, as practicable. To clearly illustrate this interchangeability of hardware and software, example components, blocks, elements, modules, circuits, and steps have been described hereby generally in terms of their functionality. Whether such functionality is implemented as hardware or software depends upon the particular application and design constraints imposed on an overall system. Skilled artisans can implement the described functionality in different ways for each particular application, but such implementation decisions should not be interpreted as causing a departure from the scope of the present disclosure. In addition, any disclosure of components contained within other components should be considered example in nature since many other architectures can be implemented to achieve the same functionality.

At least a portion of the methods, sequences, algorithms or a combination thereof which are described in connection with the examples disclosed hereby can be embodied directly in hardware, in instructions executed by a processor (e.g., a processor described hereby), or in a combination thereof. In an example, a processor includes multiple discrete hardware components. Instructions can reside in a non-transient storage medium (e.g., a memory device), such as a random-access memory (RAM), a flash memory, a read-only memory (ROM), an erasable programmable read-only memory (EPROM), an electrically erasable programmable read-only memory (EEPROM), a register, a hard disk, a removable disk, a compact disc read-only memory (CD-ROM), any other form of storage medium, the like, or a combination thereof. An example storage medium (e.g., a memory device) can be coupled to the processor so the processor can read information from the storage medium, write information to the storage medium, or both. In an example, the storage medium can be integral with the processor.

Further, examples provided hereby are described in terms of sequences of actions to be performed by, for example, one or more elements of a computing device. The actions described hereby can be performed by a specific circuit (e.g., an application specific integrated circuit (ASIC)), by instructions being executed by one or more processors, or by a combination of both. Additionally, a sequence of actions described hereby can be entirely within any form of non-transitory computer-readable storage medium having stored thereby a corresponding set of computer instructions which, upon execution, cause an associated processor (such as a special-purpose processor) to perform at least a portion of a function described hereby. Additionally, a sequence of actions described hereby can be entirely within any form of non-transitory computer-readable storage medium having stored thereby a corresponding set of instructions which, upon execution, configure the processor to create specific logic circuits. Thus, examples may be in a number of different forms, all of which have been contemplated to be within the scope of the disclosure. In addition, for each of the examples described hereby, a corresponding electrical circuit of any such examples may be described hereby as, for example, "a logic circuit configured to" perform a described action.

In an example, when a general-purpose computer (e.g., a processor) is configured to perform at least a portion of a method described hereby, then the general-purpose computer becomes a special-purpose computer which is not generic and is not a general-purpose computer. In an example, loading a general-purpose computer with special programming can cause the general-purpose computer to be configured to perform at least a portion of a method described hereby. In an example, a combination of two or more related method steps disclosed hereby forms a sufficient algorithm. In an example, a sufficient algorithm constitutes special programming. In an example, special programming constitutes any software which can cause a computer (e.g., a general-purpose computer, a special-purpose computer, etc.) to be configured to perform one or more functions, features, steps algorithms, blocks, or a combination thereof, as disclosed hereby.

At least one example provided hereby can include a non-transitory (i.e., a non-transient) machine-readable medium and/or a non-transitory (i.e., a non-transient) computer-readable medium storing processor-executable instructions configured to cause a processor (e.g., a special-purpose processor) to transform the processor and any other cooperating devices into a machine (e.g., a special-purpose processor) configured to perform at least a part of a function described hereby, at least a part of a method described hereby, the like, or a combination thereof. Performing at least a part of a function described hereby can include initiating at least a part of a function described hereby, at least a part of a method described hereby, the like, or a combination thereof. In an example, execution of the stored instructions can transform a processor and any other cooperating devices into at least a part of an apparatus described hereby. A non-transitory (i.e., a non-transient) machine-readable medium specifically excludes a transitory propagating signal. Further, one or more examples can include a computer-readable medium embodying at least a part of a function described hereby, at least a part of a method described hereby, the like, or a combination thereof.

Nothing stated or depicted in this application is intended to dedicate any component, step, block, element, feature, object, benefit, advantage, or equivalent to the public, regardless of whether the component, step, block, element, feature, object, benefit, advantage, or the equivalent is recited in the claims. While this disclosure describes examples, changes and modifications can be made to the examples disclosed hereby without departing from the scope defined by the appended claims. A feature from any of the provided examples can be used in combination with one another feature from any of the provided examples in accordance with the general principles described hereby. The present disclosure is not intended to be limited to the specifically disclosed examples alone.

What is claimed is:

1. A computer-implemented method for environment-adaptive robotic disinfecting, at least a portion of the method being performed by a computing device comprising at least one physical processor, the method comprising:
   initiating creating a map, in three dimensions and from digital images, of at least a portion of a structure;
   initiating identifying a first location, from the digital images, of a robot in the structure;
   initiating segmenting, by the physical processor and using a machine learning-based classifying algorithm, the digital images to identify potentially contaminated surfaces located in the at least the portion of the structure, wherein the machine learning-based classifying algorithm is trained with training data including:
      images of object surfaces known to be potentially contaminated; and
      respective predictor weights that are:
         respectively associated with the images of the object surfaces; and
         based on object affordance information identifying respective levels of potential contamination of the object surfaces depicted in the images of the object surfaces known to be potentially contaminated;
   initiating creating a map of the potentially contaminated surfaces within the structure;
   initiating calculating a trajectory of movement of at least a portion of the robot to move the at least the portion of the robot to a location of at least a portion of the potentially contaminated surfaces, wherein the trajectory of movement is calculated from the map of the at least the portion of the structure, the first location of the robot in the structure, and the map of the potentially contaminated surfaces within the structure; and
   initiating movement by the at least the portion of the robot along the trajectory of movement to position a directional decontaminant source adjacent to the location of the at least the portion of the potentially contaminated surfaces.

2. The computer-implemented method of claim 1, further comprising initiating training the machine learning-based classifying algorithm with the training data.

3. The computer-implemented method of claim 2, wherein the training data includes digital information describing images of object surfaces known to be potentially contaminated in the at least the portion of the structure.

4. The computer-implemented method of claim 1, wherein:
   the trajectory of the movement is configured to move the robot from the first location of the robot in the structure to a second location of the robot in the structure; and
   the second location of the robot in the structure is within an effective disinfecting range of the directional decontaminant source relative to at least one potentially contaminated surface in the potentially contaminated surfaces.

5. The computer-implemented method of claim 1, wherein the calculating the trajectory of the movement of the at least the portion of the robot further comprises calculating the trajectory of the movement from digital information indicating waypoints along a path to be following by an end-effector of the robot.

6. The computer-implemented method of claim 1, further comprising receiving a user input directing the robot to at least one of:
   disinfect a specific area in the structure; or
   perform the initiating creating the map of the at least the portion of the structure at a specific time.

7. The computer-implemented method of claim 1, further comprising:
   receiving information indicating present physical contact between a human and the robot; and
   initiating stopping, responsive to the information indicating present physical contact, the movement by the at least the portion of the robot.

8. An apparatus configured to perform environment-adaptive robotic disinfecting, comprising:
   a physical processor; and
   a memory communicably coupled to the physical processor and storing instructions configured to cause the physical processor to:
      initiate creating a map, in three dimensions and from digital images, of at least a portion of a structure;
      initiate identifying a first location, from the digital images, of a robot in the structure;
      initiate segmenting, using a machine learning-based classifying algorithm, the digital images to identify potentially contaminated surfaces located in the at least the portion of the structure, wherein the machine learning-based classifying algorithm is trained with training data including:
         images of object surfaces known to be potentially contaminated; and
         respective predictor weights that are:
            respectively associated with the images of the object surfaces; and
            based on object affordance information identifying respective levels of potential contamination of the object surfaces depicted in the images of the object surfaces known to be potentially contaminated;
      initiate creating a map of the potentially contaminated surfaces within the structure;
      initiate calculating a trajectory of movement of at least a portion of the robot to move the at least the portion of the robot to a location of at least a portion of the potentially contaminated surfaces, wherein the trajectory of movement is calculated from the map of the at least the portion of the structure, the first location of the robot in the structure, and the map of the potentially contaminated surfaces within the structure; and
      initiate movement by the at least the portion of the robot along the trajectory of movement to position a directional decontaminant source adjacent to the location of the at least the portion of the potentially contaminated surfaces.

9. The apparatus of claim 8, wherein the memory further stores instructions configured to cause the processor to initiate training the machine learning-based classifying algorithm with the training data.

10. The apparatus of claim 9, wherein the training data includes digital information describing images of object surfaces known to be potentially contaminated in the at least the portion of the structure.

11. The apparatus of claim 8, wherein:
the trajectory of the movement is configured to move the robot from the first location of the robot in the structure to a second location of the robot in the structure; and
the second location of the robot in the structure is within an effective disinfecting range of the directional decontaminant source relative to at least one potentially contaminated surface in the potentially contaminated surfaces.

12. The apparatus of claim 8, wherein the calculating the trajectory of the movement of the at least the portion of the robot further comprises calculating the trajectory of the movement from digital information indicating waypoints along a path to be following by an end-effector of the robot.

13. The apparatus of claim 8, wherein the memory further stores instructions configured to cause the processor to receive a user input directing the robot to at least one of:
disinfect a specific area in the structure; or
perform the initiating creating the map of the at least the portion of the structure at a specific time.

14. The apparatus of claim 8, wherein the memory further stores instructions configured to cause the processor to:
receive information indicating present physical contact between a human and the robot; and
initiate stopping, responsive to the information indicating present physical contact, the movement by the at least the portion of the robot.

15. The apparatus of claim 8, wherein the physical processor is at least one of a microprocessor, a microcontroller, a digital signal processor, a field programmable gate array, a programmable logic device, an application-specific integrated circuit, a controller, a non-generic special-purpose processor, a state machine, a gated logic device, a discrete hardware component, or a dedicated hardware finite state machine.

16. A non-transitory computer-readable medium, comprising processor-executable instructions stored thereon configured to cause a processor to:
initiate creating a map, in three dimensions and from digital images, of at least a portion of a structure;
initiate identifying a first location, from the digital images, of a robot in the structure;
initiate segmenting, using a machine learning-based classifying algorithm, the digital images to identify potentially contaminated surfaces located in the at least the portion of the structure,
wherein the machine learning-based classifying algorithm is trained with training data including:
images of object surfaces known to be potentially contaminated; and
respective predictor weights that are:
respectively associated with the images of the object surfaces; and
based on object affordance information identifying respective levels of potential contamination of the object surfaces depicted in the images of the object surfaces known to be potentially contaminated;
initiate creating a map of the potentially contaminated surfaces within the structure;
initiate calculating a trajectory of movement of at least a portion of the robot to move the at least the portion of the robot to a location of at least a portion of the potentially contaminated surfaces,
wherein the trajectory of movement is calculated from the map of the at least the portion of the structure, the first location of the robot in the structure, and the map of the potentially contaminated surfaces within the structure; and
initiate movement by the at least the portion of the robot along the trajectory of movement to position a directional decontaminant source adjacent to the location of the at least the portion of the potentially contaminated surfaces.

17. The non-transitory computer-readable medium of claim 16, wherein the processor-executable instructions further include instructions configured to cause the processor to initiate training the machine learning-based classifying algorithm with the training data.

18. The non-transitory computer-readable medium of claim 17, wherein the training data includes digital information describing images of object surfaces known to be potentially contaminated in the at least the portion of the structure.

19. The non-transitory computer-readable medium of claim 16, wherein:
the trajectory of the movement is configured to move the robot from the first location of the robot in the structure to a second location of the robot in the structure; and
the second location of the robot in the structure is within an effective disinfecting range of the directional decontaminant source relative to at least one potentially contaminated surface in the potentially contaminated surfaces.

20. The non-transitory computer-readable medium of claim 16, wherein the calculating the trajectory of the movement of the at least the portion of the robot further comprises calculating the trajectory of the movement from digital information indicating waypoints along a path to be following by an end-effector of the robot.

21. The non-transitory computer-readable medium of claim 16, wherein the processor-executable instructions further include instructions configured to cause the processor to receive a user input directing the robot to at least one of:
disinfect a specific area in the structure; or
perform the initiating creating the map of the at least the portion of the structure at a specific time.

22. The non-transitory computer-readable medium of claim 16, wherein the processor-executable instructions further include instructions configured to cause the processor to:
receive information indicating present physical contact between a human and the robot; and
initiate stopping, responsive to the information indicating present physical contact, the movement by the at least the portion of the robot.

* * * * *